United States Patent

Boller et al.

[11] Patent Number: 5,230,826
[45] Date of Patent: * Jul. 27, 1993

[54] HALOBENZENE LIQUID CRYSTALS

[75] Inventors: Arthur Boller, Binningen; Richard Buchecker, Zurich; Martin Schadt, Seltisberg; Alois Villiger, Basle, all of Switzerland

[73] Assignee: Hoffmann-La Roche Inc., Nutley, N.J.

[ * ] Notice: The portion of the term of this patent subsequent to Apr. 7, 2009 has been disclaimed.

[21] Appl. No.: 262,652

[22] Filed: Oct. 26, 1988

[30] Foreign Application Priority Data

Nov. 6, 1987 [CH] Switzerland .................. 4344/87
Aug. 18, 1988 [CH] Switzerland .................. 3080/88

[51] Int. Cl.$^5$ ............... C09K 19/34; C09K 19/30; G02F 1/13; C07C 69/76
[52] U.S. Cl. ................ 252/299.61; 252/299.63; 252/299.67; 359/103; 560/65; 560/102; 568/631; 568/647; 544/298; 544/244; 546/187; 546/275; 549/369; 549/370
[58] Field of Search ............ 560/65, 102; 544/298, 544/244; 546/275, 187; 549/369, 370; 252/299.61, 299.62, 299.63; 359/103

[56] References Cited

U.S. PATENT DOCUMENTS

| | | | |
|---|---|---|---|
| 4,302,352 | 11/1981 | Eidenschunk et al. | 252/299.61 |
| 4,405,488 | 9/1983 | Sugimori et al. | 252/299.61 |
| 4,473,487 | 9/1984 | Roomer et al. | 252/299.61 |
| 4,502,974 | 3/1985 | Sugimori et al. | 252/299.63 |
| 4,558,151 | 10/1985 | Takatsu et al. | 252/299.63 |
| 4,565,425 | 1/1986 | Petrzilka et al. | 252/299.61 |
| 4,621,901 | 11/1986 | Petrzilka et al. | 252/299.63 |

(List continued on next page.)

FOREIGN PATENT DOCUMENTS

| | | | |
|---|---|---|---|
| 14840 | 9/1980 | European Pat. Off. | 252/299.61 |
| 123907 | 7/1984 | European Pat. Off. | 252/299.61 |
| 168683 | 1/1986 | European Pat. Off. | 252/299.63 |
| 242716 | 10/1987 | European Pat. Off. | 252/299.63 |

(List continued on next page.)

Primary Examiner—Robert L. Stoll
Assistant Examiner—C. Harris
Attorney, Agent, or Firm—George M. Gould; George W. Johnston

[57] ABSTRACT

Compounds of the formula

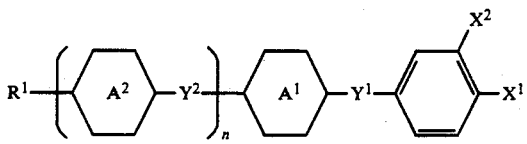

wherein $X^1$ denotes fluorine or chlorine and $X^2$ denotes hydrogen, fluorine or chlorine; $R^1$ is 3E-alkenyl,4-alkenyl, 2E-alkenyloxy or 3-alkenyloxy; n stands for the number 0 or 1; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and rings $A^1$ and $A^2$ each individually are substituted or unsubstituted trans-1,4-cyclohexylene, in which optionally 2 non-adjacent CH$_2$ groups are replaced by oxygen, or substituted or unsubstituted 1,4-phenylene, in which optionally 1 CH group or 2 CH groups is/are replaced by nitrogen; with the proviso that $X^2$ denotes fluorine or chlorine and/or $Y^1$ or $Y^2$ denotes —CH$_2$O— or —OCH$_2$— when simultaneously $X^1$ is fluorine and $R^1$ is 3E-alkenyl, and their use for liquid crystalline mixtures and electro-optical purposes.

9 Claims, No Drawings

U.S. PATENT DOCUMENTS

| | | | |
|---|---|---|---|
| 4,676,604 | 6/1987 | Petrzilka et al. | 252/299.61 |
| 4,701,547 | 10/1987 | Sugimori et al. | 560/102 |
| 4,709,030 | 11/1987 | Petrzilka et al. | 252/299.61 |
| 4,758,373 | 4/1988 | Praefcke et al. | 252/299.6 |
| 4,770,503 | 9/1988 | Buchecker et al. | 359/104 X |
| 4,776,973 | 10/1988 | Bofinger et al. | 252/299.61 |
| 4,886,621 | 12/1989 | Sage et al. | 252/299.61 |
| 4,894,181 | 1/1990 | Praefcke et al. | 252/299.61 |
| 4,985,583 | 1/1991 | Eidenschink et al. | 558/431 |
| 5,013,477 | 5/1991 | Buchecker et al. | 252/299.63 |
| 5,102,578 | 4/1992 | Buchecker et al. | 252/299.63 |

FOREIGN PATENT DOCUMENTS

| | | | |
|---|---|---|---|
| 3139130 | 5/1982 | Fed. Rep. of Germany | 252/299.63 |
| 3233641 | 3/1983 | Fed. Rep. of Germany | 252/299.63 |
| 3151356 | 7/1983 | Fed. Rep. of Germany | 252/299.63 |
| 3339218 | 5/1984 | Fed. Rep. of Germany | 252/299.61 |
| 3608764 | 3/1986 | Fed. Rep. of Germany | |
| 3631611 | 4/1988 | Fed. Rep. of Germany | 252/299.61 |
| 3631611 | 4/1988 | Fed. Rep. of Germany | 252/299.61 |
| 57-54148 | 3/1982 | Japan | 252/299.63 |
| 57-118538 | 7/1982 | Japan | 252/299.63 |
| 57-139074 | 8/1982 | Japan | 252/299.63 |
| 59-10533 | 1/1984 | Japan | 252/299.63 |
| 59-82382 | 5/1984 | Japan | 252/299.63 |
| 59-193848 | 11/1984 | Japan | 252/299.61 |
| 59-193850 | 11/1984 | Japan | 252/299.63 |
| 59-210048 | 11/1984 | Japan | 252/299.63 |
| 60-13731 | 1/1985 | Japan | 252/299.61 |
| 60-41638 | 5/1985 | Japan | 252/299.61 |
| 60-97925 | 5/1985 | Japan | 252/299.61 |
| 60-130542 | 7/1985 | Japan | 252/299.01 |
| 60-161941 | 8/1985 | Japan | 252/299.01 |
| 59-193880 | 11/1985 | Japan | |
| 2179039 | 2/1987 | United Kingdom | |

HALOBENZENE LIQUID CRYSTALS

BACKGROUND

1. Field of the Invention

The present invention is concerned with novel halobenzene derivatives, liquid crystalline mixtures which contain these compounds as well as their use for electro-optical purposes.

2. Description

Liquid crystals are used primarily as dielectrics in indicating devices, since the optical properties of such substances can be influenced by an applied voltage. Electro-optical devices based on liquid crystals are well-known to the person skilled in the art and can be based on various effects. Examples of such devices are cells having dynamic scattering, DAP cells (deformation of aligned phases), guest/hose cells, TN cells having a twisted nematic structure, STN cells ("super-twisted nematic"), SBE cells ("super-birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, the liquid crystal materials should have a low viscosity and should give short response times, low threshold potentials and a high contrast in the cells. Furthermore, at usual operating temperatures from about $-30°$ C. to about $+80°$ C., especially from about $-20°$ C. to about $+60°$ C., they should have a suitable mesophase, for example a nematic or cholesteric mesophase for the above-mentioned cells. Further properties such as the electrical conductivity, the dielectric anisotropy and the optical anisotropy must fulfill different requirements depending on the type of cell and field of application. For example, materials for cells having a twisted nematic structure should have a positive dielectric anisotropy and an electrical conductivity which is as low as possible. In addition to the general interest in compounds having a high optical anisotropy, there has recently been an increased interest in materials having a low optical anisotropy, especially for actively addressed liquid crystal indicators, for example, for TFT applications ("thin film transistor") in television sets, whereby, however, effects such as the occurrence of highly ordered smetic phases or an increase in the threshold potential and in the response times, which are frequently observed in such materials, should be avoided as far as possible.

Since liquid crystals are generally used as mixtures of several components, it is important that the components have a good miscibility with one another.

SUMMARY OF THE INVENTION

The present invention provides halobenzene derivatives of the formula

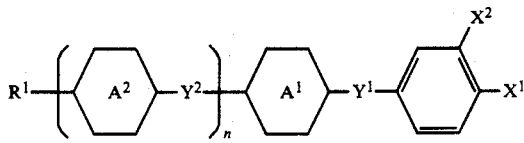

wherein $X^1$ denotes fluorine or chlorine and $X^2$ denotes hydrogen, fluorine or chlorine; $R^1$ is 3E-alkenyl, 4-alkenyl, 2E-alkenyloxy or 3-alkenyloxy; n stands for the number 0 or 1; one of the groups $Y^1$ and $Y^2$ is a single covalent bond, $-COO-$, $-OOC-$, $-CH_2CH_2-$, $-CH_2O-$ or $-OCH_2-$ and the other of the groups $Y^1$ and $Y^2$ is a single covalent bond; and rings $A^1$ and $A^2$ each individually are substituted or unsubstituted trans-1,4-cyclohexylene, in which optionally 2 non-adjacent $CH_2$ groups are replaced by oxygen, or substituted or unsubstituted 1,4-phenylene, in which optionally 1 CH group or 2 CH groups is/are replaced by nitrogen; with the proviso that $X^2$ denotes fluorine or chlorine and/or $Y^1$ or $Y^2$ denotes $-CH_2O-$ or $-OCH_2-$ when simultaneously $X^1$ is fluorine and $R^1$ is 3E-alkenyl.

The compounds in accordance with the invention generally have a positive dielectric anisotropy. Although in comparison to cyano compounds they are relatively less polar, they give amazingly low threshold potentials which are often lower than those of cyano compounds. Further, they have a high stability and a lower electrical conductivity than the cyano compounds.

Surprisingly, the compounds in accordance with the invention give, in addition to the low threshold potentials, simultaneously short response times. Highly ordered smectic phases are completely or at least largely suppressed, and the melting points are often lowered.

The compounds in accordance with the invention are therefore especially suitable as components of nematic and cholesteric mixtures. The bicyclic compounds of formula I are primarily suitable as doping agents for producing especially low threshold potentials, response times and melting points. The tricyclic compounds of formula I generally have a broad nematic or cholesteric mesophase range and are suitable for producing broad mesophase ranges in mixtures, whereby simultaneously the threshold potentials and response times remain amazingly low.

By virtue of the good solubility of the compounds of formula I with one another and in known liquid crystals comparatively high concentrations can generally be used and at the same time the number of components in liquid crystalline mixtures can be reduced. This is especially true also for the tricyclic compounds of formula I.

The optical anisotropy of the compounds of formula I can vary in a wide range depending on the choice of rings $A^1$ and $B^1$, with saturated rings leading to low values of the optical anisotropy and aromatic rings leading to high values of the optical anisotropy. The advantages mentioned above apply in the entire range and are found especially also in the compounds having a low optical anisotropy.

DETAILED DESCRIPTION OF THE INVENTION

The present invention is directed toward halobenzene derivatives of the formula

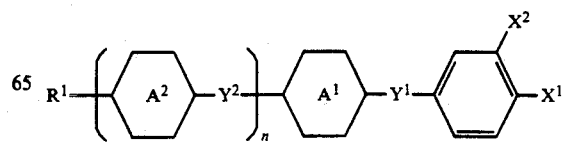

wherein $X^1$ is fluorine or chlorine and $X^2$ is hydrogen, fluorine or chlorine; $R^1$ is 3E-alkenyl, 4-alkenyl, 2E-alkenyloxy or 3-alkenyloxy; n is the integer 0 or 1; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and each of rings $A^1$ and $A^2$ individually is trans-1,4-cyclohexylene, trans-1,4-cyclohexylene in which 2 non-adjacent CH$_2$ groups are replaced by oxygen, 1,4-phenylene, or 1,4-phenylene in which 1 CH group of 2 CH groups is/are replaced by nitrogen, the above substituents for rings $A^1$ and $A^2$ being unsubstituted or substituted with at least one of cyano, lower alkyl or halo; with the proviso that $X^2$ is fluorine or chlorine and/or $Y^1$ or $Y^2$ is —CH$_2$O— or —OCH$_2$— when simultaneously $X^1$ is fluorine and $R^1$ is 3E-alkenyl.

The terms "3E-alkenyl", "4-alkenyl", "2E-alkenyloxy" and "3-alkenyloxy" in formula I embrace straight-chain and branched residues. There are generally preferred the straight-chain residues such as 3-butenyl, 3E-pentenyl, 3E-hexenyl, 3E-heptenyl, 3E-octenyl, 3E-nonenyl, 3E-decenyl, 4-pentenyl, 4-hexenyl, 4-heptenyl, 4-oxtenyl, 4-nonenyl, 4-decenyl, allyloxy, 2E-butenyloxy, 2E-pentenyloxy, 2E-hexenyloxy, 2E-heptenyloxy, 2E-octenyloxy, 2E-nonenyloxy, 3-butenyloxy, 3-pentenyloxy, 3-hexenyloxy, 3-heptenyloxy, 3-octenyloxy, 3-nonenyloxy and the like. Compounds having a branched optically active residue $R^1$ such as for example, 5-methyl-3E-heptenyl and 6-methyl-4-oxtenyl are primarily of interest as chiral doping agents and/or cholesteric liquid crystals. In the case of 4-alkenyl and 3-alkenyloxy residues $R^1$, which can be present in the E- or Z-form, the Z-form is generally preferred. Conveniently, the 3E-alkenyl residues have about 4-15 carbon atoms, the 4-alkenyl residues have about 5-15 carbon atoms, the 2E-alkenyloxy residues have about 3-14 carbon atoms and the 3-alkenyloxy residues have about 4-14 carbon atoms. Alkenyl residues with up to 10 carbon atoms and alkenyloxy residues with up to 9 carbon atoms are generally preferred. Especially preferred residues $R^1$ are 3-butenyl, 3E-pentenyl, 4-pentenyl, allyloxy and 3-butenyloxy.

The term "substituted or unsubstituted trans-1,4-cyclohexylene in which optionally 2 non-adjacent CH$_2$ groups are replaced by oxygen" (also denoted in the scope of the present invention as "saturated ring") embraces especially trans-1,4-cyclohexylene and trans-m-dioxane-2,5-diyl as well as rings which are substituted with conventional substituents usual in liquid crystals such as cyano, lower alkyl (e.g. methyl), or halo (e.g. fluorine or chlorine), for example 1-cyano-trans-1,4-cyclohexylene or 2-methyl-trans-1,4-cyclohexylene.

The term csubstituted or unsubstituted 1,4-phenylene in which optionally 1 CH group or 2 CH groups is/are replaced by nitrogen" (also denoted in the scope of the present invention as "aromatic ring") embraces especially 1,4-phenylene, pyridine-2,5-diyl, pyrazine-2,5-diyl and pyrimidine-2,5-diyl as well as rings which are substituted with conventional substituents which are usual in liquid crystals such as cyano, lower alkyl (e.g. methyl), or halo (e.g. fluorine or chlorine), for example 2-cyano-1,4-phenylene, 2-fluoro-1,4-phenylene, 2-chloro-1,4-phenylene or 2-methyl-1,4-phenylene.

The term "halo" denotes fluoro, chloro, bromo and iodo. The term "lower alkyl" denotes straight or branched chain saturated hydrocarbon groups of 1 to 4 carbon atoms.

In general, compounds of formula I with unsubstituted rings $A^1$ and $A^2$ are preferred. However, if desired, the dielectric anisotropy, the mesophase range, the solubility and the like can be modified by using substituted rings.

Formula I embraces the compounds of the following formulas

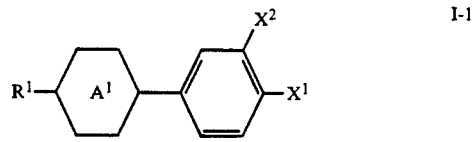

I-1

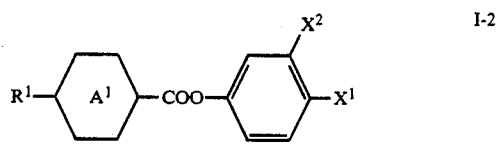

I-2

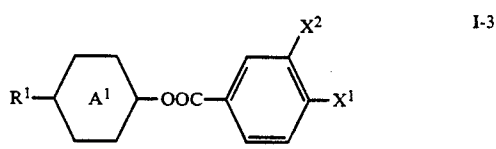

I-3

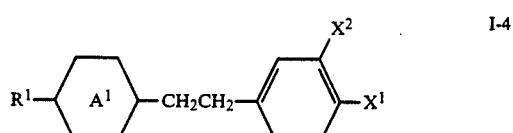

I-4

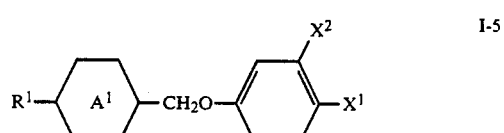

I-5

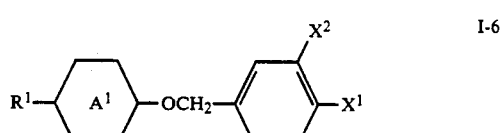

I-6

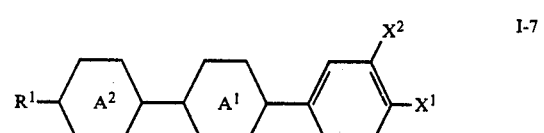

I-7

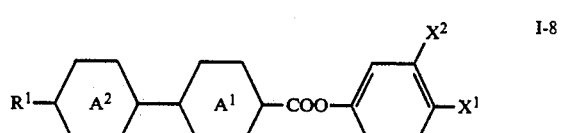

I-8

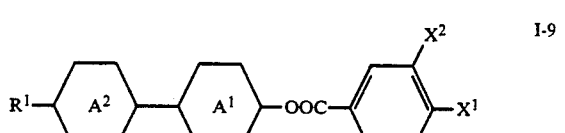

I-9

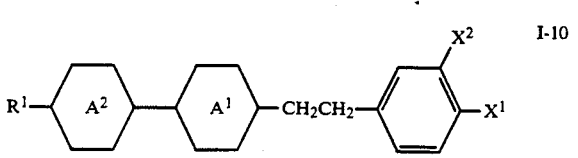

I-10

-continued

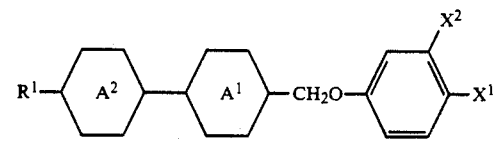
I-11

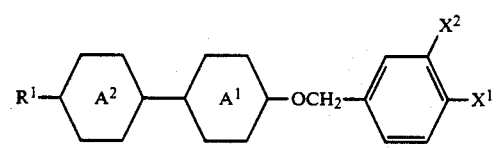
I-12

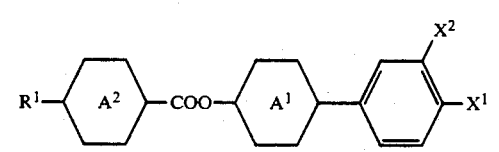
I-13

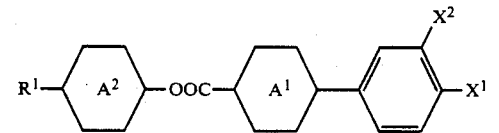
I-14

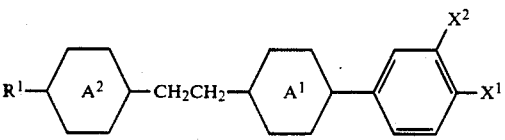
I-15

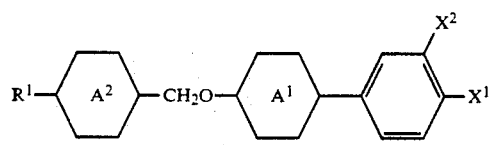
I-16

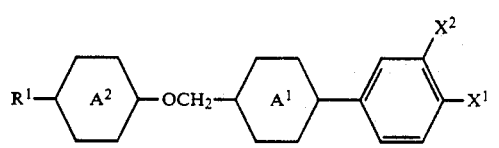
I-17 wherein $R^1$, $X^1$, $X^2$ and rings $A^1$ and $A^2$ in each case having the above significances.

In the above formulas I, I-7 and I-8 to I-17 ring $A^2$ preferably stands for substituted or unsubstituted trans-1,4-cyclohexylene, for substituted or unsubstituted 1,4-phenylene or, when ring $A^1$ is substituted or unsubstituted trans-1,4-cyclohexylene or substituted or unsubstituted 1,4-phenylene, also for pyrimidine-2,5-diyl or trans-m-dioxane-2,5-diyl. Those compounds in which ring $A^2$ stands for trans-1,4-cyclohexylene are generally especially preferred. A trans-m-dioxane-2,5-diyl group which is optionally present as ring $A^2$ is preferably linked with $R^1$ in the 5-position; in this case ring $A^1$ preferably denotes trans-1,4-cyclohexylene.

Further, in the above formulas I and I-1 to I-17 ring $A^1$ in each case preferably stands for substituted or unsubstituted trans-1,4-cyclohexylene, for substituted or unsubstituted 1,4-phenylene or for pyridine-2,5-diyl, pyrimidine-2,5-diyl or pyrazine-2,5-diyl. Of the compounds of formulas I, I-17 and I-8 to I-17 there are generally especially preferred those in which ring $A^1$ has one of the mentioned preferred significances and denotes especially an unsubstituted group and ring $A^2$ simultaneously is trans-1,4-cyclohexylene.

Examples of preferred groups of compounds of formula I are the compounds of the formulas

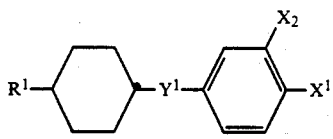
I-18

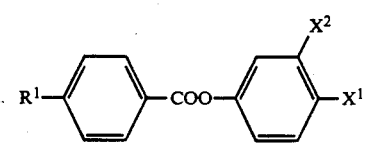
I-19

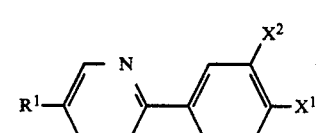
I-20

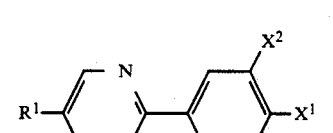
I-21

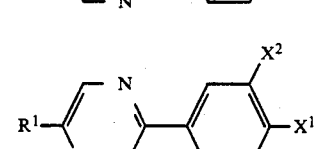
I-22

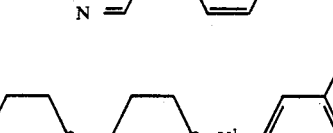
I-23

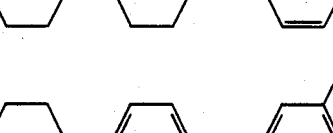
I-24

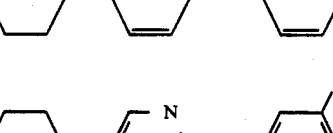
I-25

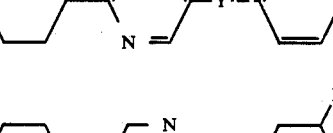
I-26

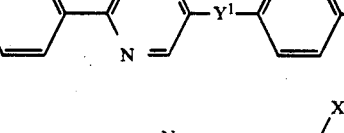
I-27

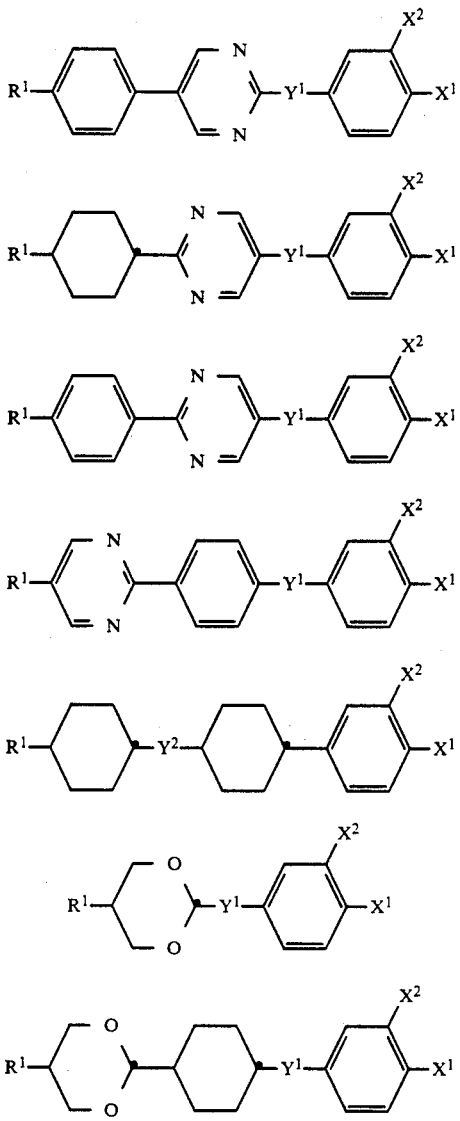

wherein $R^1$, $X^1$, $X^2$, $Y^1$ and $Y^2$ have the above significances.

Of the compounds of the above formulas I, I-1 to I-32, I-33 and I-34 there are generally preferred those in which in each case $X^1$ is fluorine and $X^2$ is hydrogen or $X^1$ and $X^2$ are fluorine or $X^1$ is chlorine and $X^2$ is hydrogen. Further, of the compounds of formulas I-18, I-23 to I-32. I-33 and I-34 there are generally preferred those in which in each case $Y^1$ is a single covalent bond or —COO—. Preferred residues $R^1$ in the above formulas I and I-1 to I-34 are 3-butenyl, 3E-pentenyl and 4-pentenyl.

The compounds of formula I can be prepared in a manner known per se, for example according to the methods described in EP-A-122389, EP-A-167912 and EP-A-168683, and in U.S. Pat. No. 4,676,604, U.S. Pat. No. 4,621,901 and U.S. patent application Ser. No. 53778/87.

The compounds of formula I in which $R^1$ is 2E-alkenyloxy or 3-alkenyloxy are generally obtained most easily by etherifying the corresponding hydroxy compound with a 2E-alkenyl halide or a 3-alkenyl halide, preferably a 2E-alkenyl bromide or a 2E-alkenyl iodide, respectively, a 3-alkenyl bromide or 3-alkenyl iodide.

The required hydroxy compounds are known or are analogues of known compounds.

The compounds of formula I in which $R^1$ is 3E-alkenyl or 4-alkenyl are generally obtained by reacting the corresponding propionaldehyde or butyraldehyde in the presence of a strong base with an alkyl-triarylphosphonium halide, preferably with an alkyl-triphenylphosphonium chloride or with an alkyl-triphenylphosphonium bromide. The reaction can be effected under the conditions which are usual for Wittig reactions. The required propionaldehydes and butyraldehydes can be obtained from the corresponding compounds having a formyl-substituted ring (derivatives of cyclohexancarboxaldehyde, benzaldehyde etc) or the corresponding cyclic ketones (cyclohexanone derivatives) by successive chain lengthening via the acetaldehydes. The chain lengthening can be effected for example, in each case by a Wittig reaction with a methoxymethyl-triphenylphosphonium chloride, and subsequent hydrolysis (for example with acetic acid). Further, a chain lengthening by 3 carbon atoms can also be effected for example, by a Wittig reaction with a 2-(1,3-dioxolan-2-yl)ethyl-triarylphosphonium halide, preferably 2-(1,3-dioxolan-2-yl)ethyl-triphenylphosphonium bromide, subsequent catalytic hydrogenation of the C-C double bond and hydrolysis of the dioxolane ring, for example, with acetic acid. The latter method has, moreover, the advantage that, prior to the hydrolysis of the dioxolane ring, other functional groups can, if desired, be introduced readily into the molecule or converted.

When the central portion of formula I has a group which can be formed readily by a final linkage such as, for example, an ester group or methyleneoxy group for $Y^1$ or $Y^2$ or a dioxane ring for ring $A^1$ and $A^2$, it can be advantageous to prepare the corresponding educt (for example, carboxylic acid, hydroxy compound, halo compound, 1,3-diol, aldehyde) containing the alkenyl group or the alkenyloxy group in an analogous manner to the methods described above. Subsequently, for example, the carboxylic acid obtained can be esterified with a suitable hydroxy compound (to give a compound of formula I in which $Y^1$ or $Y^2$ is —COO—), or the hydroxy compound obtained can be esterified with a suitable carboxylic acid or a suitable carboxylic acid chloride (to give a compound of formula I in which $Y^1$ or $Y^2$ is —OOC—), or a hydroxy compound obtained can be etherified with a suitable halo compound (especially a bromo or iodo compound) (to give a compound of formula I in which $Y^1$ or $Y^2$ is —OCH$_2$—) or a halo compound obtained (especially a bromo or iodo compound) can be etherified with a suitable hydroxy compound (to give a compound of formula I in which $Y^1$ or $Y^2$ is —CH$_2$O—) or a 1,3-diol obtained can be reacted with a suitable aldehyde or an aldehyde obtained can be reacted with a suitable 1,3-diol (to give a compound of formula I in which ring $A^1$ or $A^2$ is trans-m-dioxane-2,5-diyl).

The indicated reactions can be effected in each case in a manner known per se. The required starting materials are known or can be prepared in a manner known per se. The above synthesis variants and the reaction conditions are illustrated further in the Synthesis Examples.

The compounds of formula I can be used in the form of mixtures with one another and/or with other liquid crystal components such as for example, with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to the person skilled in the art and many of them are, moreover, commercially available.

The liquid crystalline mixtures in accordance with the invention contain at least two components, of which as least one component is a compound of formula I. A second component and optionally further components can be further compounds of formula I or other liquid crystal components. The compounds of formula I are especially suitable for nematic mixtures or, insofar as at least one component of the mixture is optically active, also for cholesteric mixtures.

The compounds of formula I in which n stands for the number 0 and $R^1$ is 4-alkenyl are generally advantageously used together with other nematic or cholesteric materials, for example together with tricyclic compounds of formula I. The mixtures in accordance with the invention therefore preferably contain one or more compounds of formula I and a nematic or cholesteric carrier material.

Having regard to the good solubility of the compounds of formula I and having regard to their good miscibility with one another, their amount in the mixtures in accordance with the invention can be relatively high. However, an amount of 1-50 wt. %, especially about 5-30 wt. %, of compounds of formula I is generally preferred.

The mixtures in accordance with the invention preferably contain in addition to one or more compounds of formula I one or more compounds from the group of compounds of the formula wherein $R^2$ and $R^7$ each are alkyl, 1E-alkenyl, 3E-alkenyl or 4-alkenyl; $R^3$ is cyano, —NCS, alkyl, 1E-alkenyl, 3E-alkenyl, 4-alkenyl, alkoxy 2E-alkenyloxy or 3-alkenyloxy; $R^4$ is alkyl, 3E-alkenyl or 4-alkenyl; $R^5$ is cyano, —NCS, alkyl, 3E-alkenyl, or 4-alkenyl, alkoxy, 2-E-alkenyloxy or 3-alkenyloxy; $R^6$ is cyano, alkyl, 3E-alkenyl, 4-alkenyl, alkoxy, 2E-alkenyloxy or 3-alkenyloxy; Z is a single covalent bond or —CH$_2$CH$_2$—; $R^8$ is cyano, alkoxy, 2E-alkenyloxy, 3-alkenyloxy, alkyl, 1E-alkenyl, 3E-alkenyl or 4-alkenyl; $R^9$ denotes alkyl, 1E-alkenyl or, when one of the groups $Y^1$ and $Y^2$ is a single covalent bond, —COO—, —OOC— or —CH$_2$CH$_2$— and the other of the groups $Y^1$ and $Y^2$ is a single covalent bond, also 3E-alkenyl; and n, $Y^1$, $Y^2$ and rings $A^1$ and $A^2$ have the above significances.

The alkyl, alkenyl, alkoxy and alkenyloxy residues $R^2$-$R^9$ in formulas II–XIV are preferably straight-chain residues. They preferably have up to 12, particularly up to 7, carbon atoms.

The compounds of formula XI in which $R^2$ is 1E-alkenyl, 3E-alkenyl or 4-alkenyl are novel. They can be prepared according to the methods illustrated in the Synthesis Examples.

The mixtures in accordance with the invention can also contain optically active compounds (for example, optically active 4'-alkyl- or 4'-alkoxy-4-biphenylcarbonitriles) and/or dichroic coloring substances (for example, azo, azoxy or anthraquinone coloring substances). The amount of such compounds is determined by the solubility, the desired pitch, colour, extinction and the like. The amount of optically active compounds and dichroic coloring substances generally amounts to in each case a mixture of about 10 wt. % in the total mixture.

The preparation of the mixtures in accordance with the invention and the preparation of the electro-optical devices can be effected in a manner known per se.

The preparation of the compounds of formula I and the novel compounds of formula XI as well as liquid crystalline mixtures containing these compounds are illustrated further by the following Examples. C is a crystalline phase, $S_B$ is a smectic B phase, N is a nematic phase and I is the isotropic phase, $V_{10}$ and $V_{50}$ denote respectively the voltage for 10% and 50% transmission, $p=(V_{50}-V_{10})/V_{10}$ is a measurement of the steepness of the transmission curve, $t_{on}$ and $t_{off}$ denote respectively the switching-on time and the switching-off time and $\Delta n$ denotes the optical anisotropy. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C.), normal pressure is about 1 atmosphere and room temperature is about 23° C. The petroleum ether is a well-known mixture of low-boiling hydrocarbons. Unless indicated otherwise, the examples were carried out as written.

EXAMPLE 1 a) A solution of 1.71 g of trans-4-[trans-4-(4-pentenyl)-cyclohexyl]-cyclohexanecarbonitrile (prepared according to Example 2) in 30 ml if diethylene glycol was treated with 3.11 g of potassium hydroxide and stirred at 130° C. for 3 hours. The mixture was then poured on to ice-water, acidified with 25 percent hydrochloric acid and extracted three times with diethyl ether. The organic phases were combined, washed three times with water, dried over magnesium sulfate and evaporated. Recrystallization of the brown, crystalline residue (1.74 g) from 30 ml of hexane gave 996 mg of trans-4-[trans-4-(4-pentenyl)cyclohexyl]cyclohexanecarboxylic acid as yellowish crystals.

b) A solution of 996 mg of trans-4-[trans-4-(4-pentenyl)-cyclohexyl]cyclohexanecarboxylic acid in 80 ml of methylene chloride was treated with 752 mg of p-fluorophenol, 61 mg of 4-(dimethylamino)pyridine and 1.03 g of dicyclohexylcarbodiimide and stirred at room temperature for 15 hours. The reaction mixture was subsequently filtered. The filtrate was evaporated and the residue obtained was purified by chromatography on silica gel with ethyl acetate/petroleum ether (vol. 3:97). Crystallization of the produce obtained (1.24 g) from 40 ml of hexane gave 757 mg of pure trans-4-[trans-4-(4-pentenyl)cyclohexyl]cyclohexanecarboxylic acid 4-fluorophenyl ester with m.p. (C-N) 70.3° C. and cl.p. (N-I) 158.7° C.

The following compounds can be prepared in an analogous manner:

trans-4-(4-Pentenyl)cyclohexanecarboxylic acid 4-fluorophenyl ester, m.p. 31.3° C.;

trans-4-(4-pentenyl)cyclohexanecarboxylic acid 3,4-difluorophenyl ester, m.p. 12.4° C.;

trans-4-(4-pentenyl)cyclohexanecarboxylic acid 4-chlorophenyl ester;

4-(4-pentenyl)benzoic acid 4-fluorophenyl ester;

4-(4-pentenyl)benzoic acid 3,4-difluorophenyl ester;

4-(3-butenyloxy)benzoic acid 4-fluorophenyl ester, m.p. 65° C.;

4-(3-butenyloxy)benzoic acid 3,4-difluorophenyl ester, m.p. 47.5° C.;

4-(3-butenyloxy)benzoic acid 4-chlorophenyl ester;

trans-4-[trans-4-(4-pentenyl)cyclohexyl]cyclohexanecarboxylic acid 3,4-difluorophenyl ester;

trans-4-[trans-4-(4-pentenyl)cyclohexyl]cyclohexanecarboxylic acid 4-chlorophenyl ester;

trans-4-[trans-4-(4-pentenyl)cyclohexyl]cyclohexanecarboxylic acid 3-chloro-4-fluorophenyl ester;

trans-4-[trans-4-(4-pentenyl)cyclohexyl]cyclohexanecarboxylic acid 3-fluoro-4-chlorophenyl ester;

4-[trans-4-(4-pentenyl)cyclohexyl]benzoic acid 4-fluorophenyl ester;

4-[trans-4-(4-pentenyl)cyclohexyl]benzoic acid 3,4-difluorophenyl ester;

5-[trans-4-(4-pentenyl)cyclohexyl]-2-pyrimidinecarboxylic acid 4-fluorophenyl ester;

2-[trans-4-(4-pentenyl)cyclohexyl]-5-pyrimidinecarboxylic acid 4-fluorophenyl ester;

4-[5-(4-pentenyl)-2-pyrimidinyl]benzoic acid 4-fluorophenyl ester;

4-[2-(4-pentenyl)-5pyrimidinyl]benzoic acid 4-fluorophenyl ester;

trans-4-(4Z-hexenyl)cyclohexanecarboxylic acid 4-fluorophenyl ester;

trans-4-(4Z-hexenyl)cyclohexanecarboxylic acid 3,4difluorophenyl ester;

4-(3Z-pentenyloxy)benzoic acid 4-fluorophenyl ester;

trans-4-[trans-4-(4Z-hexenyl)cyclohexyl]cyclohexanecarboxylic acid 4-fluorophenyl ester;

4-[trans-4-(4Z-hexenyl)cyclohexyl]benzoic acid 4-fluorophenyl ester;

trans-4-(3-butenyl)cyclohexanecarboxylic acid 3,4-difluorophenyl ester, m.p. 42.0° C.;

trans-4-(3-butenyl)cyclohexanecarboxylic acid 4-chlorophenyl ester;

4-allyoxybenzoic acid 4-fluorophenyl ester;

4-allyloxybenzoic acid 3,4-difluorophenyl ester;

4-allyloxybenzoic acid 4-chlorophenyl ester;

trans-4-[trans-4-(2-butenyl)cyclohexyl]cyclohexanecarboxylic acid 3,4-difluorophenyl ester, m.p. (C-N) 55.1° C., cl.p. (N-I) 153.6° C.;

trans-4-[trans-4-(3-butenyl)cyclohexyl]cyclohexanecarboxylic acid 4-chlorophenyl ester, m.p. (C-N) 78.3° C., cl.p. (N-I) 213.5° C.;

trans-4-[trans-4-(3-butenyl)cyclohexyl]cyclohexanecarboxylic acid 3-chloro-4-fluorophenyl ester;

trans-4-[trans-4-(3-butenyl)cyclohexyl]cyclohexanecarboxylic acid 3-fluoro-4-chlorophenyl ester;

4-[trans-4-(3-butenyl)cyclohexyl]benzoic acid 3,4-difluorophenyl ester;

trans-4-(3E-pentenyl)cyclohexanecarboxylic acid 3,4difluorophenyl ester;

4-(2E-butenyloxy)benzoic acid 4-fluorophenyl ester.

EXAMPLE 2 a) 140.9 g of 2-(1,3-dioxolan-2-yl)ethyl-triphenylphosphonium bromide were suspended in 4.5 l of tetrahydrofuran while gassing with nitrogen and the suspension was treated at 0° C. within 5 minutes with 36.8 g of potassium tert.butylate. The orange suspension was stirred at room temperature for a further 1 hour and treated within 5 minutes with 46.1 g of 4-(4oxocyclohexyl)benzamide. The reaction mixture was stirred at room temperature for a further 4.5 hours and then concentrated in a vacuum. The yellowish crystals obtained (212.5 g) were treated with 1.2 l of diethyl ether. The mixture was stirred at room temperature for 30 minutes and then suction filtered. The residue was washed with diethyl ether and then suspended in 700 ml of water. The mixture was stirred for 15 minutes and then suction filtered. The residue was washed with water and dissolved while heating in 600 ml of dioxan. The solution was left to cool to room temperature. The separated crystals were removed by filtration under suction, washed with a small amount of dioxan and hexane and fried at 60° C. in a vacuum, whereby there were obtained 39.2 g of crystalline 4-[4-[2(-1,3-dioxolan-2-yl)ethylidene]cyclo-hexyl]benzamide with m.p. 209°–212° C. Working-up of the mother liquor (72.6 g) gave a further 7.7 g of produce and 64.2 g of a second mother liquor.

b) A mixture of 500 mg of 4-[4-[2-(1,3-dioxolan-2-yl)-ethylidene]cyclohexyl]benzamide and 20 ml of dioxan/-triethylamine (vol. 9:1) was hydrogenated by means of 500 mg of 10 percent platinum-charcoal for 2 hours. The reaction mixture was then filtered and the filtrate was evaporated. Recrystallization of the evaporation residue from 40 ml of dioxan gave 230 mg of 4-[trans-4-[2-(1,3-dioxolan-2-yl)ethyl]cyclohexyl]benzamide as colorless crystals.

c) 27 g of 4-[trans-4-[2-(1,3-dioxolan-2-yl) ethyl]cyclohexyl]benzamide were hydrogenated for 8 hours with 5 g of 5 percent ruthenium-charcoal in dioxan at 120° C. and 40 bar hydrogen. The crude produce (25 g) obtained after filtration and washing with tetrahydrofuran contained 69% of the cis isomer and 25% of the trans isomer of 4-[trans-4-[2-(1,3-dioxolan-2yl)ethyl]cyclohexyl]cyclohexanecarboxamide.

d) 42 g of crude 4-[trans-4-[2-(1,3-dioxolan-2-yl)ethyl]cyclohexyl]cyclohexanecarboxamide were suspended in 500 ml of ethylene glycol while gassing with argon and then treated with 19 g of solid potassium hydroxide. The mixture was heated to 180° C. (bath temperature) for 5 hours while stirring. After cooling the reaction mixture was poured into 500 ml of water, acidified to pH about 3 with 10 percent hydrochloric acid and extracted three times with 300 ml of methylene chloride each time. The combined organic phases were washed once with 500 ml of 1 percent hydrochloric acid and twice with 500 ml of water each time, dried over magnesium sulfate, filtered and evaporated. The dark brown crude product (41 g) was purified by chromatography on silica gel with ethyl acetate. Crystallization of the product obtained (36 g) from acetone gave 13.8 g of pure trans-4-[trans-4-(2-(1,3-dioxolan-2-yl)ethyl]cyclohexyl]cyclohexanecarboxylic acid. Working-up of the mother liquor gave a further 2.5 g of pure product.

e) 18 g of trans-4-[trans-4-(2-(1,3-dioxolan-2-yl)ethyl]-cyclohexyl]cyclohexanecarboxylic acid were dissolved in 600 ml of chloroform while gassing with argon and the solution was treated dropwise at 0° C. while stirring within 3 minutes with a solution of 7.2 ml of ethyl chloroformate in 40 ml of chloroform. The reaction solution was stirred for a further 30 minutes. Ammonia gas was then conducted into the solution during 10 minutes. The mixture was stirred at 0° C. for a further 30 minutes and then extracted twice with 300 ml of water each time. The aqueous phases were back-extracted with 100 ml of chloroform each time. The combined organic phases were dried over magnesium sulfate, filtered and evaporated. Recrystallization of the brown crystalline crude product obtained (19 g) from 800 ml of methylene chloride gave 13 g of trans-4-[trans-4-[2-(1,3-dioxolan-2-yl)ethyl]-cyclohexyl]cyclohexanecarboxamide as pale brown crystals.

f) 2.1 g of trans-4-[trans-4-[2-(1,3-dioxolan-2-yl)-ethyl]cyclohexyl]cyclohexanecarboxamide were suspended in 60 ml of dimethylformamide while gassing with argon. The suspension was treated with 1.32 ml of pyridine and 0.898 ml of methanesulfochloride and stirred at 60° C. (bath temperature) for 1.5 hours. The reaction solution was subsequently partitioned in methylene chloride and 10 percent hydrochloric acid. The aqueous phase was extracted twice with 100 ml of methylene chloride each time. The organic phases were washed twice with 100 ml of water each time, dried over magnesium sulfate, filtered and concentrated. There were thus obtained 2.5 g of trans-4-[trans-4-[2(1,3-dioxolan-2-yl)ethyl]cyclohexyl]cyclohexanecarbonitrile as yellow crystals in a purity of 96%.

g) 3.0 g of crude trans-4-[trans-4-[2-(1,3-dioxolan-2-yl)ethyl]cyclohexyl]cyclohexanecarbonitrile were suspended in 50 ml of water, 25 ml of glacial acetic acid and 10 ml of dioxan while gassing with argon and stirred at 100° C. for 1 hour. Thereafter, the reaction solution was treated with 100 ml of water. The aqueous phase was separated and extracted three times with 100 ml of diethyl ether each time. The organic phases were washed with 100 ml of dilute sodium hydrogen carbonate solution and with 100 ml of water, dried over magnesium sulfate, filtered and concentrated. Recrystallization of the yellow crystals obtained (2.25 g) from 60 ml of hexane gave 1.98 g of 3-[trans-4-(trans-4-cyanocyclohexyl)cyclohexyl]-propionaldehyde as colorless crystals.

h) 4.11 g of methoxymethyl-triphenylphosphonium chloride were suspended in 60 ml of tert.butyl methyl ether while gassing with argon and treated at room temperature within 2 minutes with 1.26 g of potassium tert.butylate. The suspension was stirred at room temperature for a further 1 hour, then cooled at 0° C. and treated dropwise within 5 minutes with a solution of 1.98 g of 3-[trans-4-(trans-4-cyanocyclohexyl)cyclohexyl]propionaldehyde in 25 ml of tert.butyl methyl ether. The reaction mixture was stirred at 0° C. for a further 45 minutes, the diluted with 100 ml of water and extracted three times with 100 ml of diethyl ether each time. The organic phases were washed twice with 100 ml of water each time, dried over magnesium sulfate, filtered and concentrated. Chromatographic purification of the crude produce (5.1 g) on silica gel at 0.5 bar with ethyl acetate/petroleum ether (vol. 5:95) gave 2.0 g of trans- 4-[trans-4-(4-methoxy-3-butenyl)cyclohexyl]cyclohexanecarbonitrile as a colorless milky oil.

i) 1.65 g of trans-4-[trans-4-(4-methoxy-3-butenyl)cyclohexyl]cyclohexanecarbonitrile were suspended in 50 ml of water, 25 ml of glacial acetic acid and 12 ml of dioxan while gassing with argon. The suspension was stirred at 80° C. (bath temperature) for 2 hours and then diluted with 50 ml of water. The aqueous phase was separated and extracted three times with 100 ml of diethyl ether each time. The organic phases were washed twice with 100 ml of water each time, then with 100 ml of saturated sodium hydrogen carbonate solution and again with 100 ml of water, then dried over magnesium sulfate, filtered and concentrated. There were thus obtained 1.5 g of 4-[trans-4-(trans-4-cyanocyclohexyl)cyclohexyl]butyraldehyde as colorless crystals.

j) 3.28 g of methyltriphenylphosphonium bromide were suspended in 40 ml of tert.butyl methyl ether while gassing with argon. The suspension was treated at room temperature within 1 minute with 962 mg of potassium tert.butylate and stirred for 1 hour. The mixture was subsequently cooled to 0° C., treated dropwise within 3 minutes with a solution of 1.5 g of 4-[trans-4-(trans-4-cyanocyclohexyl)cyclohexyl]butyraldehyde in 20 ml of tert.butyl methyl ether and stirred at 0° C. for a further 45 minutes. Thereafter, the reaction mixture was diluted with 80 ml of water and extracted three times with 100 ml of petroleum ether each time. The organic phases were washed twice with 100 ml of water each time, dried over magnesium sulfate, filtered and concentrated. Chromatographic purification of the crude produce (2.1 g) on silica gel at 0.5 bar with ethyl acetate/petroleum ether (vol. 2.98) and recrystallization from 20 ml of methanol gave 1.26 g of trans-4-[trans-4-(4-pentenyl)cyclohexyl]-cyclohexanecarbonitrile as colorless crystals with m.p. (C-$S_B$) 20.1° C., $S_B$-N 36.9° C., cl.p. (N-I) 54.8° C.

The following compounds can be prepared in an analogous manner:

trans-4-[trans-4-(4Z-Hexenyl)cyclohexyl]cyclohexanecarbonitrile;

trans-4-[trans-4-(4Z-heptenyl)cyclohexyl]cyclohexanecarbonitrile;

trans-4-[trans-4-(4Z-octenyl)cyclohexyl]cyclohexanecarbonitrile;

trans-4-[trans-4-(4Z-nonenyl)cyclohexyl]cyclohexanecarbonitrile;

trans-4-[trans-4-(4Z-decenyl)cyclohexyl]cyclohexanecarbonitrile.

The following compounds can be prepared by reacting the 3-[trans-4-(trans-4-cyanocyclohexyl)cyclohexyl]propionaldehyde, obtained in step g), in an analogous manner to step j) and if necessary E/Z isomerization in an analogous manner to Example 3k):

trans-4-[trans-4-(3-Butenyl)cyclohexyl]cyclohexanecarbonitrile; m.p. (C-N) 50.7° C., cl.p. (N-I) 82.7° C.;

trans-4-[trans-4-(3E-pentenyl)cyclohexyl]cyclohexanecarbonitrile; m.p. (C-N) 79.4° C., cl.p. (N-I) 99.5° C.;

trans-4-[trans-4-(3E-hexenyl)cyclohexyl]cyclohexanecarbonitrile;

trans-4-[trans-4-(3E-heptenyl)cyclohexyl]cyclohexanecarbonitrile;

trans-4-[trans-4-(3E-octenyl)cyclohexyl]cyclohexanecarbonitrile;

trans-4-[trans-4-(3E-nonenyl)cyclohexyl]cyclohexanecarbonitrile;

trans-4-[trans-4-(3E-decenyl)cyclohexyl]cyclohexanecarbonitrile;

The following compounds can be prepared by reacting the 4-(4-oxocyclohexyl)benzamide in an analogous manner to steps h) and i), acetalizing the 4-(trans-4-formylcyclohexyl)benzamide, obtained by crystallization, with ethylene glycol in the presence of p-toluenesulfonic acid, further reaction of the dioxolane in an analogous manner to steps c) to g), subsequent Wittig reaction in an analogous manner to step j) and if necessary E/Z isomerization in an analogous manner to Example 3k):

trans-4-(trans-4-Vinylcyclohexyl)cyclohexanecarbonitrile trans-4-[trans-4-(1E-propenyl)cyclohexyl]cyclohexanecarbonitrile;

trans-4-[trans-4-(1E-butenyl)cyclohexyl]cyclohexanecarbonitrile;

trans-4-[trans-4-(1E-pentenyl)cyclohexyl]cyclohexanecarbonitrile;

trans-4-[trans-4-(1E-hexenyl)cyclohexyl]cyclohexanecarbonitrile;

trans-4-[trans-4-(1E-heptenyl)cyclohexyl]cyclohexanecarbonitrile;

trans-4-[trans-4-(1E-octenyl)cyclohexyl]cyclohexanecarbonitrile;

trans-4-[trans-4-(1E-nonenyl)cyclohexyl]cyclohexanecarbonitrile;

trans-4-[trans-4-(1E-decenyl)cyclohexyl]cyclohexanecarbonitrile;

The following compounds can also be prepared starting from 4-[2-(4-oxocyclohexyl)ethyl]benzamide [preparable from the nitrile described in Mol. Cryst. Liq. Cryst. 131, 327 (1985)] in an analogous manner to the above method:

trans-4-[2-(trans-4-(4-Pentenyl)cyclohexyl)ethyl]cyclohexanecarbonitrile;

trans-4-[2-(trans-4-(4Z-hexenyl)cyclohexyl)ethyl]cyclohexanecarbonitrile;

trans-4-[2-(trans-4-(4Z-heptenyl)cyclohexyl)ethyl]cyclohexanecarbonitrile;

trans-4-[2-(trans-4-(4Z-octenyl)cyclohexyl)ethyl]cyclohexanecarbonitrile;

trans-4-[2-(trans-4-(4Z-nonenyl)cyclohexyl)ethyl]cyclohexanecarbonitrile;

trans-4-[2-(trans-4-(4Z-decenyl)cyclohexyl)ethyl]cyclohexanecarbonitrile;

trans-4-[2-(trans-4-(3butenyl)cyclohexyl)ethyl]cyclohexanecarbonitrile;

trans-4-[2-(trans-4-(2E-pentenyl)cyclohexyl)ethyl]cyclohexanecarbonitrile;

trans-4-[2-(trans-4-(3E-hexenyl)cyclohexyl)ethyl]cyclohexanecarbonitrile;

trans-4-[2-(trans-4-(3E-heptenyl)cyclohexyl)ethyl]cyclohexanecarbonitrile;

trans-4-[2-(trans-4-(3E-octenyl)cyclohexyl)ethyl]cyclohexanecarbonitrile;

trans-4-[2-(trans-4-(3E-nonenyl)cyclohexyl)ethyl]cyclohexanecarbonitrile;

trans-4-[2-(trans-4-(3E-decenyl)cyclohexyl)ethyl]cyclohexanecarbonitrile;

trans-4-[2-(trans-4-vinylcyclohexyl)ethyl]cyclohexanecarbonitrile;

trans-4-[2-(trans-4-(1E-propenyl)cyclohexyl)ethyl]cyclohexanecarbonitrile;

trans-4-[2-(trans-4-(1E-butenyl)cyclohexyl)ethyl]cyclohexanecarbonitrile;

trans-4-[2-(trans-4-(1E-pentenyl)cyclohexyl)ethyl]cyclohexanecarbonitrile;

trans-4-[2-(trans-4-(1E-hexenyl)cyclohexyl)ethyl]cyclohexanecarbonitrile;

trans-4-[2-(trans-4-(1E-heptenyl)cyclohexyl)ethyl]-cyclohexanecarbonitrile;

trans-4-[2-(trans-4-(1E-octenyl)cyclohexyl)ethyl]cyclohexanecarbonitrile;

trans-4-[2-(trans-4-(1E-nonenyl)cyclohexyl)ethyl]cyclohexanecarbonitrile;

trans-4-[2-(trans-4-(1E-decenyl)cyclohexyl)ethyl]cyclohexanecarbonitrile;

EXAMPLE 3 a) A suspension of 109.6 g of 4-(4-nitrophenyl)cyclohexanone (preparable by nitrating 4-phenylcyclohexanone) in 1 l of dioxan was treated with 50 ml of triethylamine and 2 g of 5 percent palladium-charcoal and hydrogenated at room temperature and 0.3 bar hydrogen pressure while stirring well. After 2 hours the mixture was filtered. The filtrate was evaporated on a water-jet vacuum at a bath temperature of 30° C. and the evaporation residue was dried at 40° C. overnight in a drying oven under a water-jet vacuum. There were thus obtained 94.5 g of 4-(4-aminophenyl)cyclohexanone as white crystals with m.p. 127°-128° C.

b) 200 ml of 4 N sulfuric acid were heated to 80° C. in a sulfonation flask and then treated with about 5% of a solution of 37.9 g of 4-(4-aminophenyl)cyclohexanone in 200 ml of 4 N sulfuric acid. Subsequently, the remaining solution of 4-(4-aminophenyl)cyclohexanone as well as a solution of 15.2 g of sodium nitrite in 45 ml of water were simultaneously added dropwise to the reaction mixture at 80° C. within 1.5 hours. Thereafter, the mixture was treated dropwise at 80° C. within 30 minutes with a solution of 9 g of sodium nitrite in 27 ml of water and stirred at 80° C. for a further 1 hour. After cooling the reaction mixture to 0° C. the separated crystals were removed by filtration under suction, washed with 200 ml of cold water and dried up to constant weight at 60° C. in a drying oven under a water-jet vacuum. The crystalline crude product (34.6 g) was suspended in 520 ml of ethyl acetate. The suspension was heated to reflux for 1 hour, then treated with 1.7 g of active carbon and then heated to reflux for a further 1 hour. The mixture was subsequently suction filtered (rinsing with 40 ml of warm ethyl acetate) and the filtrate was evaporated under a water-jet vacuum at a bath temperature of 40° C. Drying of the evaporation residue up to constant weight at 60° C. in a drying oven under a water-jet vacuum gave 32.2 g of 4-(4-hydroxyphenyl)cyclohexanone as yellow-brown crystals with m.p. 165°-166° C.

c) A suspension of 3.8 g of 4-(4-hydroxyphenyl)cyclohexanone in 60 of tert.butyl methyl ether was treated in a sulfonation flask under a weak stream of nitrogen with 10.6 g of 2-(1,3-dioxolan-2-yl)ethyl-triphenylphosphonium bromide and 2.2 g of potassium tert.butylate. The mixture was firstly stirred for 30 minutes, then treated portionwise within 2.25 hours at 25° C. with a further 2.7 g of potassium tert.butylate and stirred at room temperature for a further 1 hour. Thereafter, the reaction mixture was treated with an additional 1.8 g of 2-(1,3-dioxolan-2-yl)ethyl-triphenylphosphonium bromide and 0.45 g of potassium tert.butylate and stirred for a further 1 hour. Subsequently, the reaction mixture was poured into 80 ml of water and acidified with 11 ml of 2 N sulfuric acid. The aqueous phase was separated and extracted twice with 80 ml of tert.butyl methyl ether each time. The organic phases were washed twice with 50 ml of water each time, dried over sodium sulfate and suction filtered. The filtrate was evaporated up to constant weight under a water-jet vacuum at a bath temperature of 40° C. The reddish oil obtained (10.9 g) was separated by chromatography on silica gel with toluene and toluene/tert.butyl methyl ether (vol. 20:1). Evaporation of the product fractions in a water-jet vacuum and drying the residue up to constant weight in a drying oven under a water-jet vacuum at 60° C. finally gave 4.5 g of 4-[4-[2-(1,3-dioxolan-2-yl)ethylidene]cyclohexyl]phenol as yellowish crystals with m.p. 125.5°-126.5° C.

d) A solution of 36.5 g of 4-[4-[2-(1,3-dioxolan-2-yl)ethylidene]cyclohexyl]phenol in 500 ml of toluene and 50 ml of triethylamine was hydrogenated in a hydrogenation autoclave at 90° C. for 1 hour with 3.2 g of 5 percent platinum-charcoal and 10 bar of hydrogen. The mixture was subsequently suction filtered and the residue was washed with 30 ml of warm toluene. The filtrate was evaporated up to constant weight under a water-jet vacuum at a bath temperature of 40° C. The white crystals obtained (37 g) were dissolved in 180 ml of methanol while heating. The solution was left to cool to room temperature and then placed in a refrigerator for 5 hours. The crystals were subsequently removed by filtration under suction, washed with 50 ml of cold methanol and dried at 60° C. in a drying oven under a water-jet vacuum. There were thus obtained 27.6 g of 4-[trans-4-[2-(1,3-dioxolan-2-yl)ethyl]cyclohexyl]phenol as white crystals with m.p. 153.5°-154.5° C.

e) A mixture of 100 g of 4-[trans-4-[2-(1,3-dioxolan-2-yl)ethyl]cyclohexyl]phenol, 10 g of 5 percent rhodium-/aluminum oxide and 1 l of ethyl acetate was hydrogenated in a steel stirring autoclave with 50 bar of hydrogen at 80° C. for 90 minutes. The catalyst was then removed by filtration under suction and washed with 100 ml of ethyl acetate. The filtrate was evaporated and the residue was dried at 25° C./0.4 mbar. There were thus obtained 101.75 g of 4-[trans-4-[2-(1,3-dioxolan-2-yl)ethyl]cyclohexyl]cyclohexanol containing 59% of cis isomer and 36% of trans isomer.

f) A solution of 12.9 g of pyridinium chlorochromate in 80 ml of methylene chloride was treated dropwise within 5 minutes at room temperature while gassing with nitrogen with a solution of 13.0 g of 4-[trans-4-[2-(1,3-dioxolan-2-yl)ethyl]cyclohexyl]cyclohexanol in 40 ml of methylene chloride. The mixture was stirred for a further 1 hour, then diluted with 100 ml of diethyl ether and filtered and the filtrate was evaporated. The evaporation residue was taken up in 200 ml of diethyl ether, the mixture was filtered, the filtrate was evaporated and then this procedure was repeated twice more. Thereafter, the brownish solid mass obtained (12.1 g) was separated by chromatography on silica gel with ethyl acetate/petroleum ether (vol. 1:4). Crystallization of the colorless ketone fraction from 60 ml of ethyl acetate and 200 ml of petroleum ether finally gave 7.0 g of pure 4-[trans-4-[2-(1,3-dioxolan-2-yl)ethyl]cyclohexyl]cyclohexanone.

g) A suspension of 2.97 g of sodium borohydride in 300 ml if isopropanol was treated dropwise while gassing with nitrogen at −70° C. with a solution of 11 g of 4-[trans-4-[2-(1,3-dioxolan-2-yl)ethyl]cyclohexyl]cyclohexanone in 200 ml of isopropanol. After about 1 hour the reaction mixture was left to warm to room temperature, diluted with 500 ml of 0.1 N hydrochloric acid and extracted three times with 300 ml of methylene chloride each time. The organic phases were washed with water, dried over magnesium sulfate, filtered and evaporated. Crystallization of the residue (11 g) from 500 ml of ethyl acetate/petroleum ether (vol. 3:5) gave 6.6 g of pure trans-4-[trans-4-[2-(1,3-dioxolan-2-yl)ethyl]cyclohexyl]cyclohexanol with m.p. 129.5° C.

h) 2.04 g of sodium hydride as an about 50 percent oily suspension were placed in a round flask while gassing with nitrogen and washed twice with pentane. Then, 40 ml of dry tetrahydrofuran and a solution of 6.0 g of trans-4-[trans-4-[2-(1,3-dioxolan-2-yl)ethyl]cyclohexyl]cyclohexanol in 30 ml of tetrahydrofuran were added to the sodium hydride. The mixture was stirred at room temperature for 30 minutes, then treated with 4.0 ml of methyl iodide and heated to reflux for 2 hours. Subsequently, the reaction mixture was cooled, taken up in 200 ml of diethyl ethyl and washed three times with 200 ml of water each time. The organic phase was fried over magnesium sulfate, filtered and evaporated, whereby there were obtained 6.3 g of 2-[2-[trans-4-(trans-4-methoxycyclohexyl)cyclohexyl]ethyl]-1,3-dioxolane with m.p. 74° C.

i) 6.2 g of 2-[2-[trans-4-(trans-4-methoxycyclohexyl)cyclohexyl]ethyl]-1,3-dioxolane were treated with 100 ml of water, 50 ml of glacial acetic acid and 20 ml of dioxan while gassing with nitrogen. The mixture was stirred at 100° C. (bath temperature) for 1.5 hours, then neutralized with dilute sodium hydrogen carbonate solution and extracted three times with diethyl ether. The combined ether phases were washed once with water and twice with dilute sodium hydrogen carbonate solution, dried over magnesium sulfate, filtered and evaporated. Recrystallization of the crude aldehyde obtained (4.34 g) from 150 ml of petroleum ether at −20° C. gave 2.8 g of 3-trans-4-(trans-4-methoxycyclohexyl)cyclohexyl]propionaldehyde in a purity of 96%.

j) 2.65 g of ethyltriphenylphosphonium bromide were suspended in 40 ml of tert.butyl methyl ether while gassing with argon. The suspension was treated at room temperature with 797 mg of potassium tert.butylate and stirred for 1 hour. The mixture was subsequently cooled to 0° C., treated dropwise within 3 minutes with a solution of 1.1 g of 3-[trans-4-(trans-4-methoxycyclohexyl)cyclohexyl]propionaldehyde in 15 ml of tert.butyl methyl ether and then left to warm slowly to room temperature while stirring. After 2 hours the pale yellow suspension was partitioned in diethyl ether/water. The aqueous phase was separated and washed three times diethyl ether. The organic phases were washed twice with water, dried over magnesium sulfate, filtered and evaporated. Chromatographic purification of the yellow, solid crude product on silica gel with ethyl acetate/petroleum ether (vol. 3.97) gave 0.91 g of trans-4-(3-pentenyl)-1-(trans-4-methoxycyclohexyl)cyclohexane with a Z/E ratio of 86:11.

k) 0.91 g of trans-4-(3-pentenyl)-1-(trans-4-methoxycyclohexyl)cyclohexane (Z/E=86:11) was treated with 6 ml of toluene. 0.11 g of sodium benzenesulfinate and 1 ml of 1 N hydrochloric acid while gassing with nitrogen. The mixture was stirred at 50° C. for 15 hours, then poured into 100 ml of dilute sodium hydrogen carbonate solution and extracted three times with 50 ml of diethyl ether each time. The combined organic phases were washed with 100 ml of dilute sodium carbonate solution and with 100 ml of water, dried over magnesium sulfate, filtered and evaporated. The yellowish oil obtained (0.9 g) was purified by chromatography on silver nitrate-impregnated silica gel with diethyl ether/hexane (vol. 1:9). Recrystallization of the product obtained (486 mg) from 10 ml of methanol at −20° C. gave pure trans-4-(3E-pentenyl)-1-(trans-4-methoxycyclohexyl)cyclohexane with m.p. (C-N) 16.6° C. and cl.p. (N-I) 43.7° C.

The following compounds can be prepared in an analogous manner:

trans-4-(3-Butenyl)-1-(trans-4-methoxycyclohexyl)cyclohexane, m.p. (C-N) −13.6° C., cl.p. (N-I) 18.0° C.;

trans-4-(3-butenyl)-1-(trans-4-ethoxycyclohexyl)cyclohexane, m.p. (C-N) 13.1° C., cl.p. (N-I) 45.3° C.;

trans-4-(3-butenyl)-1-(trans-4-propyloxycyclohexyl)cyclohexane;

trans-4-(3-butenyl)-1-(trans-4-butyloxycyclohexyl)cyclohexane;

trans-4-(3-butenyl)-1-(trans-4-pentyloxycyclohexyl)cyclohexane;

trans-4-(3-butenyl)-1-(trans-4-hexyloxycyclohexyl)cyclohexane;

trans-4-(3E-pentenyl)-1-(trans-4-ethoxycyclohexyl)cyclohexane, m.p. (C-N) 44.5° C., cl.p. (N-I) 76.5° C.;

trans-4-(3E-pentenyl)-1-(trans-4-propyloxycyclohexyl)-cyclohexane;

trans-4-(3E-pentenyl)-1-(trans-4-butyloxycyclohexyl)-cyclohexane;

trans-4-(3E-pentenyl)-1-(trans-4-pentyloxycyclohexyl)-cyclohexane;

trans-4-(3E-pentenyl)-1-(trans-4-hexyloxycyclohexyl)-cyclohexane;

trans-4-(3E-pentenyl)-1-(trans-4-methoxycyclohexyl)-cyclohexane;

trans-4-(3E-hexenyl)-1-(trans-4-ethoxycyclohexyl)-cyclohexane;

trans-4-(3E-hexenyl)-1-(trans-4-propyloxycyclohexyl)-cyclohexane;

trans-4-(3E-hexenyl)-1-(trans-4-butyloxycyclohexyl)-cyclohexane;

trans-4-(3E-hexenyl)-1-(trans-4-pentyloxycyclohexyl)-cyclohexane;

trans-4-(3E-hexenyl)-1-(trans-4-hexyloxycyclohexyl)-cyclohexane.

The following compounds can be prepared in an analogous manner to steps a) to i) and further reaction of the propionaldehyde obtained in an analogous manner to Example 2, steps h), i) and j):

trans-4-(4-Pentenyl)-1-(trans-4-methoxycyclohexyl)-cyclohexane, m.p. (C-S$_B$) 7.7° C., cl.p. (S$_B$-1) 14.0° C.;

trans-4-(4-pentenyl)-1-(trans-4-ethoxycyclohexyl)cyclohexane, m.p. (C-S$_B$) 10.5° C., cl.p. (S$_B$-I) 43.1° C.;

trans-4-(4-pentenyl)-1-(trans-4-propyloxycyclohexyl)-cyclohexane;

trans-4-(4-pentenyl)-1-(trans-4-butyloxycyclohexyl)-cyclohexane;

trans-4-(4-pentenyl)-1-(trans-4-pentyloxycyclohexyl)-cyclohexane;

trans-4-(4-pentenyl)-1-(trans-4-hexyloxycyclohexyl)-cyclohexane;

trans-4-(4Z-hexenyl)-1-(trans-4-methoxycyclohexyl)-cyclohexane;

trans-4-(4Z-hexenyl)-1-(trans-4-ethoxycyclohexyl)-cyclohexane;

trans-4-(4Z-hexenyl)-1-(trans-4-propyloxycyclohexyl)-cyclohexane;

trans-4-(4Z-hexenyl)-1-(trans-4-butyloxycyclohexyl)-cyclohexane;

trans-4-(4Z-hexenyl)-1-(trans-4-pentyloxycyclohexyl)-cyclohexane;

trans-4-(4Z-hexenyl)-1-(trans-4-hexyloxycyclohexyl)-cyclohexane;

The following compounds can be prepared by reacting the 4-(4-hydroxyphenyl)cyclohexanone (step b) in an analogous manner to Example 2, steps h) and i), acetalizing the 4-(trans-4-formylcyclohexyl)phenol obtained with ethylene glycol in the presence of p-toluenesulfonic acid and further reacting the dioxolane in an analogous manner to the previous steps e) to k):

trans-4-Vinyl-1-(trans-4-methoxycyclohexyl)cyclohexane;
trans-4-vinyl-1-(trans-4-ethoxycyclohexyl)cyclohexane;
trans-4-vinyl-1-(trans-4-propyloxycyclohexyl)cyclohexane;
trans-4-vinyl-1-(trans-4-butyloxycyclohexyl)cyclohexane;
trans-4-vinyl-1-(trans-4-pentyloxycyclohexyl)cyclohexane;
trans-4-vinyl-1-(trans-4-hexyloxycyclohexyl)cyclohexane;
trans-4-(1E-propenyl)-1-(trans-4-methoxycyclohexyl)-cyclohexane;
trans-4-(1E-propenyl)-1-(trans-4-ethoxycyclohexyl)-cyclohexane;
trans-4-(1E-propenyl)-1-(trans-4-propyloxycyclohexyl)-cyclohexane;
trans-4-(1E-propenyl)-1-(trans-4-butyloxycyclohexyl)-cyclohexane;
trans-4-(1E-propenyl)-1-(trans-4-pentyloxycyclohexyl)-cyclohexane;
trans-4-(1E-propenyl)-1-(trans-4-hexyloxycyclohexyl)-cyclohexane;
trans-4-(1E-butenyl)-1-(trans-4-methoxycyclohexyl)-cyclohexane;
trans-4-(1E-butenyl)-1-(trans-4-ethoxycyclohexyl)cyclohexane;
trans-4-(1E-butenyl)-1-(trans-4-propyloxycyclohexyl)-cyclohexane;
trans-4-(1E-butenyl)-1-(trans-4-butyloxycyclohexyl)-cyclohexane;
trans-4-(1E-butenyl)-1-(trans-4-pentyloxycyclohexyl)-cyclohexane;
trans-4-(1E-pentenyl)-1-(trans-4-methoxycyclohexyl)-cyclohexane;
trans-4-(1E-pentenyl)-1-(trans-4-ethoxycyclohexyl)-cyclohexane;
trans-4-(1E-pentenyl)-1-(trans-4-propyloxycyclohexyl)-cyclohexane;
trans-4-(1E-pentenyl)-1-(trans-4-butyloxycyclohexyl)-cyclohexane;

The following compounds can also be prepared according to the above method starting from 4-(2-phenylethyl)-cyclohexanone [preparable in an analogous manner to the nitrile described in Mol. Cryst. Liq. Cryst. 131, 327 (1985)]:

4-[2-[trans-4-(2-(1,3-Dioxolan-2-yl)ethyl)cyclohexyl]-ethyl]cyclohexanone;
trans-4-(3-butenyl)-1-[2-(trans-4-methoxycyclohexyl)-ethyl]cyclohexane;
trans-4-(3-butenyl)-1-[2-(trans-4-ethoxycyclohexyl)ethyl]cyclohexane;
trans-4-(3-butenyl)-1-[2-(trans-4-propyloxycyclohexyl)-ethyl]cyclohexane;
trans-4-(3-butenyl)-1-(2-(trans-4-butyloxycyclohexyl)-ethyl]cyclohexane;
trans-4-(3-butenyl)-1-[2-(trans-4-pentyloxycyclohexyl)-ethyl]cyclohexane;
trans-4-(3-butenyl)-1-[2-(trans-4-hexyloxycyclohexyl)-ethyl]cyclohexane;
trans-4-(3E-pentenyl)-1-[2-(trans-4-methoxycyclohexyl)-ethyl]cyclohexane;
trans-4-(3E-pentenyl)-1-[2-(trans-4-ethoxycyclohexyl)-ethyl]cyclohexane;
trans-4-(3E-pentenyl)-1-[2-(trans-4-propyloxycyclohexyl)-ethyl]cyclohexane;
trans-4-(3E-pentenyl)-1-[2-(trans-4-butyloxycyclohexyl)-ethyl]cyclohexane;
trans-4-(3E-pentenyl)-1-[2-(trans-4-pentyloxycyclohexyl)-ethyl]cyclohexane;
trans-4-(3E-pentenyl)-1-[2-(trans-4-hexyloxycyclohexyl)-ethyl]cyclohexane;
trans-4-(3E-hexenyl)-1-[2-(trans-4-methoxycyclohexyl)-ethyl]cyclohexane;
trans-4-(3E-hexenyl)-1-[2-(trans-4-ethoxycyclohexyl)-ethyl]cyclohexane;
trans-4-(3E-hexenyl)-1-[2-(trans-4-propyloxycyclohexyl)-ethyl]cyclohexane;
trans-4-(3E-hexenyl)-1-[2-(trans-4-butyloxycyclohexyl)-ethyl]cyclohexane;
trans-4-(3E-hexenyl)-1-[2-(trans-4-pentyloxycyclohexyl)-ethyl]cyclohexane;
trans-4-(3E-hexenyl)-1-[2-(trans-4-hexyloxycyclohexyl)-ethyl]cyclohexane;
trans-4-(4-pentenyl)-1-[2-(trans-4-methoxycyclohexyl)-ethyl]cyclohexane;
trans-4-(4-pentenyl)-1-[2-(trans-4-ethoxycyclohexyl)-ethyl]cyclohexane;
trans-4-(4-pentenyl)-1-[2-(trans-4-propyloxycyclohexyl)-ethyl]cyclohexane;
trans-4-(4-pentenyl)-1-[2-(trans-4-butyloxycyclohexyl)-ethyl]cyclohexane;
trans-4-(4-pentenyl)-1-[2-(trans-4-pentyloxycyclohexyl)-ethyl]cyclohexane;
trans-4-(4-pentenyl)-1-[2-(trans-4-hexyloxycyclohexyl)-ethyl]cyclohexane;
trans-4-(4Z-hexenyl)-1-[2-(trans-4-methoxycyclohexyl)-ethyl]cyclohexane;
trans-4-(4Z-hexenyl)-1-[2-(trans-4-ethoxycyclohexyl)-ethyl]cyclohexane;
trans-4-(4Z-hexenyl)-1-[2-(trans-4-propyloxycyclohexyl)-ethyl]cyclohexane;
trans-4-(4Z-hexenyl)-1-[2-(trans-4-butyloxycyclohexyl)-ethyl]cyclohexane;
trans-4-vinyl-1-[2-(trans-4-methoxycyclohexyl)-ethyl]-cyclohexane;
trans-4-vinyl-1-[2-(trans-4-ethoxycyclohexyl)-ethyl]-cyclohexane;
trans-4-vinyl-1-[2-(trans-4-propyloxycyclohexyl)-ethyl]-cyclohexane;
trans-4-vinyl-1-[2-(trans-4-butyloxycyclohexyl)-ethyl]-cyclohexane;
trans-4-vinyl-1-[2-(trans-4-pentyloxycyclohexyl)-ethyl]-cyclohexane;
trans-4-vinyl-1-[2-(trans-4-hexyloxycyclohexyl)-ethyl]-cyclohexane;
trans-4-(1E-propenyl)-1-[2-(trans-4-methoxycyclohexyl)-ethyl]cyclohexane;
trans-4-(1E-propenyl)-1-[2-(trans-4-ethoxycyclohexyl)-ethyl]cyclohexane;
trans-4-(1E-propenyl)-1-[2-(trans-4-propyloxycyclohexyl)ethyl]cyclohexane;
trans-4-(1E-propenyl)-1-[2-(trans-4-butyloxycyclohexyl)-ethyl]cyclohexane;
trans-4-(1E-propenyl)-1-[2-(trans-4-pentyloxycyclohexyl)ethyl]cyclohexane;
trans-4-(1E-propenyl)-1-[2-(trans-4-hexyloxycyclohexyl)-ethyl]cyclohexane;

trans-4-(1E-butenyl)-1-[2-(trans-4-methoxycyclohexyl)-ethyl]cyclohexane;

trans-4-(1E-butenyl)-1-[2-(trans-4-ethoxycyclohexyl)-ethyl]cyclohexane;

trans-4-(1E-butenyl)-1-[2-(trans-4-propyloxycyclohexyl)-ethyl]cyclohexane;

trans-4-(1E-butenyl)-1-[2-(trans-4-butyloxycyclohexyl)-ethyl]cyclohexane;

trans-4-(1E-butenyl)-1-[2-(trans-4-pentyloxycyclohexyl)-ethyl]cyclohexane;

trans-4-(1E-pentenyl)-1-[2-(trans-4-methoxycyclohexyl)-ethyl]cyclohexane;

trans-4-(1E-pentenyl)-1-[2-(trans-4-ethoxycyclohexyl)-ethyl]cyclohexane;

trans-4-(1E-pentenyl)-1-[2-(trans-4-propyloxycyclohexyl)ethyl]cyclohexane;

trans-4-(1E-pentenyl)-1-[2-(trans-4-butyloxycyclohexyl)-ethyl]cyclohexane.

EXAMPLE 4 a) A Grignard solution from 3.56 g of magnesium and 16.75 ml of 1-bromo-4-fluorobenzene in 70 ml of tetrahydrofuran was treated dropwise at 0° C. within 30 minutes with a solution of 33.1 g of 4-[trans-4-[2-(1,3-dioxolan-2-yl)ethyl]cyclohexyl]cyclohexanone (prepared according to Example 3) in 90 ml of tetrahydrofuran. The reaction mixture was stirred at room temperature for a further 4 hours and then heated to boiling for 1.5 hours. Subsequently, the reaction mixture was left to cool, diluted with 100 ml of diethyl ether and washed with 80 ml of semi-saturated ammonium chloride solution. The aqueous phase was back-extracted with 100 ml of diethyl ether. The combined organic phases were washed three times with 60 ml of saturated sodium chloride solution each time, dried over sodium sulfate, filtered and evaporated. There were thus obtained 41.0 g of crude 1-[4-[trans-4-(2-(1,3-dioxolan- 2-yl)ethyl]cyclohexyl]-1-hydroxycyclohexyl]-4-fluorobenzene.

b) A solution of 41.0 g of crude 1-[4-[trans-4-(2-(1,3-dioxolan-2-yl)ethyl]cyclohexyl]-1-hydroxycyclohexyl]-4-fluorobenzene in 225 ml of m-xylene was treated with 15 g of potassium hydrogen sulfate and the mixture was heated to boiling for 11 hours while stirring. After cooling the salt was removed by filtration. The filtrate was diluted with 250 ml of diethyl ether, washed with 200 ml of saturated sodium hydrogen carbonate solution and washed twice with 150 ml of water each time, dried over sodium sulfate and concentrated. There were thus obtained 30.3 g of crude 1-[4-[trans-4-(2-(1,3-dioxolan-2-yl)ethyl)cyclohexyl]-1-cyclohexenyl]-4-fluorobenzene.

c) A solution of 31.5 g of crude 1-[4-[trans-4-(2-(1,3-dioxolan-2-yl)ethyl]cyclohexyl]-1-cyclohexenyl]-4-fluorobenzene and 0.5 ml of triethylamine in 1 l of toluene was hydrogenated at room temperature and normal pressure with 4.5 g of 5 percent palladium-charcoal until the hydrogen uptake came to a standstill. The catalyst was removed by filtration and the filtrate was evaporated. For the isomerization, the resulting 1-[4-[trans-4-(2-(1,3-dioxolan-2-yl)ethyl)-cyclohexyl]cyclohexyl]-4-fluorobenzene (31.1 g; cis/trans ratio about 1:1) was treated with a solution of 10.0 g of potassium tert.butylate in 310 ml of N,N-dimethylformamide and heated to 105° C. for 23 hours. Subsequently, the reaction mixture was poured on to 400 g of ice and 100 ml of saturated sodium hydrogen carbonate solution. The mixture was extracted once with 500 ml of diethyl ether and twice with 250 ml of diethyl ether each time. The organic phases were washed three times with 200 ml of water each time, dried over sodium sulfate, filtered and evaporated. There were thus obtained 30.5 g of predominantly solid 1-[trans-4-[trans-4-(2-(1,3-dioxolan-2-yl)ethyl)cyclohexyl]cyclohexyl]-4-fluorobenzene which was further processed without additional purification.

The following compounds can be prepared in an analogous manner:

1-[trans-4-[trans-4-(2-(1,3-Dioxolan-2-yl)ethyl)cyclohexyl]cyclohexyl]-3,4-difluorobenzene;

1-[trans-4-[trans-4-(2-(1,3-dioxolan-2-yl)ethyl)cyclohexyl]cyclohexyl]-3-chloro-4-fluorobenzene;

1-[trans-4-[trans-4-(2-(1,3-dioxolan-2-yl)ethyl)cyclohexyl]cyclohexyl]-3-fluoro-4-chlorobenzene;

1-[trans-4-[trans-4-(2-(1,3-dioxolan-2-yl)ethyl)cyclohexyl]cyclohexyl]-4-chlorobenzene;

1-[trans-4-[2-[trans-4-(2-(1,3-dioxolan-2-yl)ethyl)-cyclohexyl]ethyl]cyclohexyl]-4-fluorobenzene;

1-[trans-4-[2-[trans-4-(2-(1,3-dioxolan-2-yl)ethyl)-cyclohexyl]ethyl]cyclohexyl]-3,4-difluorobenzene;

1-[trans-4-[2-[trans-4-(2-(1,3-dioxolan-2-yl)ethyl)-cyclohexyl]ethyl]cyclohexyl]-3-chloro-4-fluorobenzene;

1-[trans-4-[2-[trans-4-(2-(1,3-dioxolan-2-yl)ethyl)-cyclohexyl]ethyl]cyclohexyl]-4-chlorobenzene;

1-[trans-4-[2-[trans-4-(2-(1,3-dioxolan-2-yl)ethyl)-cyclohexyl]ethyl]cyclohexyl]-3-fluoro-4-chlorobenzene.

EXAMPLE 5 a) A solution of 3.1 g of trans-4-[trans-4-[2-(1,3-dioxolan-2-yl)ethyl]cyclohexyl]cyclohexanecarboxylic acid (prepared according to Example 2) in 50 ml of dry diethyl ether is treated at 0° C. with 380 mg of lithium aluminium hydride and then heated to reflux for 4 hours. Thereafter, the reaction mixture is cooled, treated with ice-water and ammonium chloride solution and extracted with diethyl ether. The organic phase is washed with water, dried over magnesium sulfate, filtered and evaporated. The resulting crude product of [trans-4-[trans-4-(2-(1,3-dioxolan-2-yl)-ethyl)cyclohexyl]cyclohexyl]methanol is used without additional purification.

b) A solution of 2.96 g of crude [trans-4-[trans-4-(2-(1,3-dioxolan-2-yl)ethyl)cyclohexyl]cyclohexyl]methanol in 20 ml of dry pyridine is treated at 0° C. with 2.1 g of p-toluenesulfonyl chloride. The mixture is stirred at room temperature for 15 hours, then diluted with 200 ml methylene chloride and washed several times with water. The organic phase is fried over magnesium sulfate, filtered and evaporated. Chromatographic purification of the resulting crude product on silica gel with ethyl acetate/petroleum ether (vol. 1:9) gives [trans-4-]trans-4-(2-(1,3-dioxolan-2-yl)ethyl)cyclohexyl]cyclohexyl]methyl p-toluenesulfonate.

c) A solution of 0.?3 g of potassium hydroxide in 7 ml of 95 percent ethanol is treated with 1.12 g of p-fluorophenol. Thereafter, the mixture is treated with a solution of 2.26 g of [trans-4-[trans-4-(2-(1,3-dioxolan-2-yl)-ethyl)cyclohexyl]cyclohexyl]methyl p-toluenesulfonate in 23 ml of ethanol and stirred at 80° C. (bath temperature) for 24 hours. Subsequently, the reaction mixture is partitioned in 1 N hydrochloric acid and methylene chloride. The organic phase is washed several times with water, dried over magnesium sulfate, filtered and evaporated. Chromatographic purification of the resulting crude product on silica gel with ethyl acetate/petroleum ether gives 1-[[trans-4-(trans-4-(2-(1,3-dioxolan- 2-yl)-ethyl)cyclohexyl]cyclohexyl]methoxy]-4-fluorobenzene.

The following compounds can be prepared in an analogous manner:

1-[[trans-4-(trans-4-(2-(1,3-Dioxolan-2-yl)-ethyl)cyclohexyl)cyclohexyl]methoxy]-3,4-difluorobenzene;

1-[[trans-4-(trans-4-(2-(1,3-dioxolan-2-yl)-ethyl)cyclohexyl)cyclohexyl]methoxy]-3-chloro-4-fluorobenzene;

1-[[trans-4-(trans-4-(2-(1,3-dioxolan-2-yl)-ethyl)cyclohexyl)cyclohexyl]methoxy]-4-chlorobenzene;

1-[[trans-4-(trans-4-(2-(1,3-dioxolan-2-yl)-ethyl)cyclohexyl)cyclohexyl]methoxy]-3-fluoro-4-chlorobenzene.

EXAMPLE 6 a) A solution of 3.1 g of pyridinium chlorochromate in 20 ml of methylene chloride is treated dropwise at room temperature with a solution of 3 g of [trans-4-[trans-4-(2-(1,3-dioxolan-2-yl)ethyl)cyclohexyl]cyclohexyl]methanol (preparable according to Example 5) in 10 ml of methylene chloride. The mixture is stirred for a further 1 hour, then diluted with 50 ml of diethyl ether and filtered. The filtrate is evaporated, the evaporation residue is taken up in 50 ml of diethyl ether and the solution obtained is again filtered. Chromatographic purification on silica gel with ethyl acetate/hexane finally gives trans-4-[trans-4-[2-(1,3-dioxolan-2-yl)ethyl]-cyclohexyl]cyclohexanecarboxaldehyde.

b) 3 g of p-fluorobenzyl-triphenylphosphonium bromide (preparable from p-fluorobenzyl bromide and triphenylphosphine) are suspended in 50 ml of tert.butyl methyl ether. The suspension is treated at room temperature with 0.75 g of potassium tert.butylate and stirred for 1.5 hours. Subsequently, the mixture is treated dropwise at 0° C. within 5 minutes with a solution of 1.40 g of trans-4-[trans-4-[2-(1,3-dioxolan-2-yl)ethyl]cyclohexyl]cyclohexanecarboxaldehyde in 25 ml of tert.butyl methyl ether and stirred at room temperature for a further 24 hours. Thereafter, the reaction mixture is taken up diethyl ether, washed several times with water, dried over magensium sulfate, filtered and concentrated. Chromatographic purification of the resulting crude product on silica gel with ethyl acetate/petroleum ether (vol. 3:97) gives β-[trans-4-[trans-4-(2-(1,3-dioxolan-2-yl)ethyl)cyclohexyl]cyclohexyl]-4-fluorostyrene.

c) A solution of 1 g of β-[trans-4-[trans-4-(2-(1,3-dioxolan-2-yl)ethyl)cyclohexyl]cyclohexyl]-4-fluorostyrene in 10 ml of toluene and 5 ml of ethanol is hydrogenated with 500 mg of 5 percent palladium-charcoal at room temperature and normal pressure until the hydrogen uptake comes to a standstill. The black suspension is subsequently filtered. Evaporation of the filtrate gives 1-[2-[trans-4-[trans-4-(2-(1,3-dioxolan-2-yl)ethyl)cyclohexyl]cyclohexyl]ethyl]-4-fluorobenzene.

The following compounds can be prepared in an analogous manner:

1-[2-[trans-4-[trans-4-(2-(1,3-Dioxolan-2-yl)ethyl)cyclohexyl)cyclohexyl]ethyl]-3,4-difluorobenzene; 1-[2-[trans-4-[trans-4-(2-(1,3-dioxolan-2-yl)ethyl)cyclohexyl)cyclohexyl]ethyl]-3-chloro-4-fluorobenzene; 1-[2-[trans-4-[trans-4-(2-(1,3-dioxolan-2-yl)ethyl)cyclohexyl)cyclohexyl]ethyl]-4-chlorobenzene; 1-[2-[trans-4-[trans-4-(2-(1,3-dioxolan-2-yl)ethyl)-cyclohexyl]cyclohexyl]ethyl]-3-fluoro-4-chlorobenzene.

EXAMPLE 7

A solution of 1.7 g of 4-fluorobenzoyl chloride in 5 ml of pyridine is treated with 2.8 g of trans-4-[trans-4-(2-(1,3-dioxolan-2-yl)ethyl]cyclohexyl]-cyclohexyl (prepared according to Example 3) and stirred at room temperature for 12 hours. Thereafter, the reaction mixture is poured on to ice-water and extracted three times with diethyl ether. The organic phases are washed in succession with saturated sodium hydrogen carbonate solution, with 10 percent hydrochloric acid, with saturated sodium hydrogen carbonate solution and with water, then dried over magnesium sulfate, filtered and concentrated. Chromatographic purification of the resulting crude product on silica gel with ethyl acetate/petroleum ether (vol. 3:97) gives 4-fluorobenzoic acid trans-4-[trans-4-(2-(1,3-dioxolan-2-yl)ethyl]cyclohexyl]-cyclohexyl ester.

The following compounds can be prepared in an analogous manner:

3,4-Difluorobenzoic acid trans-4-[trans-4-[2-(1,3-dioxolan-2-yl)ethyl]cyclohexyl]cyclohexyl ester;

3-chloro-4-fluorobenzoic acid trans-4-[trans-4-(2-(1,3-dioxolan-2-yl)ethyl]cyclohexyl]cyclohexyl ester;

4-chlorobenzoic acid trans-4-[trans-4-[2-(1,3-dioxolan-2-yl)ethyl]cyclohexyl]cyclohexyl ester;

3-fluoro-4-chlorobenzoic acid trans-4-[trans-4-[2-(1,3-dioxolan-2-yl)ethyl]cyclohexyl]cyclohexyl ester.

EXAMPLE 8

2.04 g of sodium hydride as an about 50% oily suspension are placed under nitrogen gasification and washed twice with pentane. There are then added to the sodium hydride 40 ml of dry tetrahydrofuran and a solution of 6.0 g of trans-4-[trans-4-[2-(1,3-dioxolan-2-yl)ethyl]-cyclohexyl]cyclohexyl (prepared according to Example 2) in 30 ml of tetrahydrofuran. The mixture is stirred at room temperature for 30 minutes, then treated with 6.03 g of 4-fluorobenzyl bromide and heated to reflux for 2 hours. Subsequently, the reaction mixture is cooled, taken up in 200 ml of diethyl ether and washed three times with 200 ml of water each time. The organic phase is dried over magnesium sulfate, filtered and evaporated, whereby there is obtained trans-4-[trans-4-[2-(1,3-dioxolan-2-yl)-ethyl]cyclohexyl]cyclohexyl 4-fluorobenzyl ether.

The following compounds can be prepared in an analogous manner:

trans-4-[trans-4-[2-(1,3Dioxolan-2-yl)ethyl]cyclohexyl]cyclohexyl 3,4-difluorobenzyl ether;

trans-4-[trans-4-[2-(1,3-dioxolan-2-yl)ethyl]cyclohexyl]cyclohexyl 3-chloro-4-fluorobenzyl ether;

trans-4-[trans-4-[2-(1,3-dioxolan-2-yl)ethyl]cyclohexyl]cyclohexyl 4-chlorobenzyl ether;

trans-4-[trans-4-[2-(1,3-dioxolan-2-yl)ethyl]cyclohexyl]cyclohexyl 3-fluoro-4-chlorobenzyl ether.

EXAMPLE 9 a) A mixture of 29.1 g of crude 1-trans-4-[trans-4-(2-(1,3-dioxolan-2-yl)ethyl)cyclohexyl]cyclohexyl]-4-fluorobenzene, 200 ml of dioxan, 200 ml of glacial acetic acid and 400 ml of water was heated to slight boiling (bath temperature 115° C.) for 15 hours while stirring and gassing with nitrogen. The reaction mixture was then poured on to 500 g of ice. The aqueous phase was separated and extracted three times with 400 ml of diethyl ether each time. The combined organic phases were washed with 500 ml of saturated sodium hydrogen carbonate solution and with 500 ml of water, dried over sodium sulfate, filtered and concentrated. There were thus obtained 25.2 g of crude, solid 3-[trans-4-[trans-4-(4-fluorophenyl)cyclohexyl]-cyclohexyl]propionaldehyde.

b) A suspension of 9.1 g of methoxymethyl-triphenylphosphonium chloride in 50 ml of diethyl ether was treated with 2.85 g of potassium tert.butylate while gassing with nitrogen. The red suspension was stirred at room temperature for a further 30 minutes and then treated dropwise at 0° C. with a solution of 5.43 g of crude 3-[trans-4-[trans-4-(4-fluorophenyl)cyclohexyl]cyclohexyl]propionaldehyde in 30 ml of dry diethyl ether. The reaction mixture was stirred at room temperature for a further 90 minutes, then poured into 300 ml of hexane and filtered. Chromatographic purification of the concentrated filtrate on silica gel with hexane gave 4.9 g of solid 1-[trans-4-[trans-4-(4-methoxy-3-butenyl)-cyclohexyl]cyclohexyl]-4-fluorobenzene.

c) A mixture of 2.48 g of 1-[trans-4-[trans-4-(4-methoxy-3-butenyl)cyclohexyl]cyclohexyl]-4-fluorobenzene, by 30 ml of dioxan, 20 ml of glacial acetic acid and 40 ml of water was heated to slight boiling (bath temperature 115° C.) while stirring and gassing with nitrogen. After cooling the suspension was diluted with 70 ml of water. The aqueous phase was separated and extracted three times with 80 ml of diethyl ether each time. The combined organic phases were washed twice with 1000 ml of water each time, dried over sodium sulfate, filtered and concentrated. There were thus obtained 2.3 g of solid 4-[trans-4-[trans-4-(4-fluorophenyl)-cyclohexyl]cyclohexyl]butyraldehyde.

d) A suspension of 5.19 g of methyl-triphenylphosphonium bromide in 80 ml of diethyl ether was treated with 1.55 g of potassium tert.butylate while gassing with nitrogen. The yellow suspension was stirred at room temperature for a further 45 minutes and then treated dropwise at 0° C. with a solution of 2.3 g of 4-[trans-4-[trans-4-(4-fluorophenyl)cyclohexyl]cyclohexyl]butyraldehyde. The reaction mixture was stirred at 0° C. for a further 2 hours and then diluted with 60 ml of water. The aqueous phase was separated and extracted twice with 60 ml of hexane each time. The combined organic phases were washed neutral with water, dried over sodium sulfate, filtered and concentrated. Chromatographic purification of the residue on silica gel with hexane gave 1.89 g of crude product. After two-fold recrystallization from acetone at −20° C. there were obtained 1.22 g of 1-[trans-4-[trans-4-(4-pentenyl)-cyclohexyl]cyclohexyl]-4-fluorobenzene with m.p. (C-N) 65.7° C. and cl.p. (N-I) 129.7° C.

The 4-alkenyl compounds named in Example 1 as well as the following compounds can be prepared in an analogous manner:

1-[trans-4-[trans-4-(4-Pentenyl)cyclohexyl]cyclohexyl3,4-difluorobenzene;
1-[trans-4-[trans-4-(4-pentenyl)cyclohexyl]cyclohexyl-3-chloro-4-fluorobenzene;
1-[trans-4-[trans-4-(4-pentenyl)cyclohexyl]cyclohexyl-4-chlorobenzene;
1-[trans-4-[trans-4-(4-pentenyl)cyclohexyl]cyclohexyl-3-fluoro-4-chlorobenzene;
1-[trans-4-[2-(trans-4-(4-pentenyl)cyclohexyl)ethyl]-cyclohexyl]-4-fluorobenzene;
1-[trans-4-[2-(trans-4-(4-pentenyl)cyclohexyl)ethyl]-cyclohexyl]-3,4-difluorobenzene;
1-[trans-4-[2-(trans-4-(4-pentenyl)cyclohexyl)ethyl]-cyclohexyl]-3-chloro-4-fluorobenzene;
1-[trans-4-[2-(trans-4-(4-pentenyl)cyclohexyl)ethyl]-cyclohexyl]-4-chlorobenzene;
1-[trans-4-[2-(trans-4-(4-pentenyl)cyclohexyl)ethyl]-cyclohexyl]-3-fluoro-4-chlorobenzene;
1-[[trans-4-(trans-4-(4-pentenyl)cyclohexyl)cyclohexyl]-methoxy]-4-fluorobenzene;
1-[[trans-4-(trans-4-(4-pentenyl)cyclohexyl)cyclohexyl]-methoxy]-3,4-difluorobenzene;
1-[[trans-4-(trans-4-(4-pentenyl)cyclohexyl)cyclohexyl]-methoxy]-3-chloro-4-fluorobenzene;
1-[[trans-4-(trans-4-(4-pentenyl)cyclohexyl)cyclohexyl]-methoxy]-4-chlorobenzene;
1-[[trans-4-(trans-4-(4-pentenyl)cyclohexyl)cyclohexyl]-methoxy]-3-fluoro-4-chlorobenzene;
1-[2-[trans-4-(trans-4-(4-pentenyl)cyclohexyl)cyclohexyl]ethyl]-4-fluorobenzene; m.p. (C-S$_B$) 7.1° C., phase transition (S$_B$-N) 93° C,. cl.p. (N-I) 116.6° C.;
1-[2-[trans-4-(trans-4-(4-pentenyl)cyclohexyl)cyclohexyl]ethyl]-3,4-difluorobenzene;
1-[2-[trans-4-(trans-4-(4-pentenyl)cyclohexyl)cyclohexyl]ethyl]-3-chloro-4-fluorobenzene;
1-[2-[trans-4-(trans-4-(4-pentenyl)cyclohexyl)cyclohexyl]ethyl]-4-chlorobenzene;
1-[2-[trans-4-(trans-4-(4-pentenyl)cyclohexyl)cyclohexyl]ethyl]-3-fluoro-4-chlorobenzene;
4-fluorobenzoic acid trans-4-[trans-4-(4-pentenyl)-cyclohexyl]cyclohexyl ester;
3,4-difluorobenzoic acid trans-4-[trans-4-(4-pentenyl)-cyclohexyl]cyclohexyl ester;
3-chloro-4-fluorobenzoic acid trans-4-[trans-4-(4-pentenyl)-cyclohexyl]cyclohexyl ester;
4-chlorobenzoic acid trans-4-[trans-4-(4-pentenyl)-cyclohexyl]cyclohexyl ester;
3-fluoro-4-chlorobenzoic acid trans-4-[trans-4-(4-pentenyl)-cyclohexyl]cyclohexyl ester;
trans-4-[trans-4-(4-pentenyl)-cyclohexyl]cyclohexyl 4-fluorobenzyl ether;
trans-4-[trans-4-(4-pentenyl)-cyclohexyl]cyclohexyl 3,4-difluorobenzyl ether;
trans-4-[trans-4-(4-pentenyl)-cyclohexyl]cyclohexyl 3-chloro-4-fluorobenzyl ether;
trans-4-[trans-4-(4-pentenyl)-cyclohexyl]cyclohexyl 4-chlorobenzyl ether;
trans-4-[trans-4-(4-pentenyl)-cyclohexyl]cyclohexyl 3-fluoro-4-chlorobenzyl ether;
1-[trans-4-[trans-4-(4Z-hexenyl)cyclohexyl]cyclohexyl]-4-fluorobenzene;
1-[trans-4-[trans-4-(4Z-hexenyl)cyclohexyl]cyclohexyl]-3,4-difluorobenzene;
1-[trans-4-[2-(trans-4-(4Z-hexenyl)cyclohexyl)ethyl]-cyclohexyl]-4-fluorobenzene;
1-[trans-4-[2-(trans-4-(4Z-hexenyl)cyclohexyl)ethyl]-cyclohexyl]-3,4-difluorobenzene;
1-[[trans-4-(trans-4-(4Z-hexenyl)cyclohexyl)cyclohexyl]-methoxy]-4-fluorobenzene;
1-[[trans-4-(trans-4-(4Z-hexenyl)cyclohexyl)cyclohexyl]-methoxy]-3,4difluorobenzene;
1-[2-[trans-4-(trans-4-(4Z-hexenyl)cyclohexyl)cyclohexyl]ethyl]-4-fluorobenzene;
1-[2-[trans-4-(trans-4-(4Z-hexenyl)cyclohexyl)cyclohexyl]ethyl]-3,4-difluorobenzene;
4-fluorobenzoic acid trans-4-[trans-4-(4Z-hexenyl)-cyclohexyl]cyclohexyl ester;
3,4-difluorobenzoic acid trans-4-[trans-4-(4Z-hexenyl)-cyclohexyl]cyclohexyl ester;
trans-4-[trans-4-(4Z-hexenyl)cyclohexyl]cyclohexyl 4-fluorobenzyl ether;

trans-4-[trans-4-(4Z-hexenyl)-cyclohexyl]cyclohexyl 3,4-difluorobenzyl ether;

The 3E-alkenyl compounds named in Example 1 as well as the following compounds can also be prepared in an analogous manner by omitting steps b) and c):

1-[trans-4-[trans-4-(3-Butenyl)cyclohexyl]cyclohexyl-3,4difluorobenzene;

1-[trans-4-[trans-4-(3-butenyl)cyclohexyl]cyclohexyl-3-chloro-4-fluorobenzene;

1-[trans-4-[trans-4-(3-butenyl)cyclohexyl]cyclohexyl-4-chlorobenzene;

1-[trans-4-[trans-4-(3-butenyl)cyclohexyl]cyclohexyl-3-fluoro-4-chlorobenzene;

1-[trans-4-[2(trans-4-(3-butenyl)cyclohexyl)ethyl]-cyclohexyl]-3,4-difluorobenzene;

1-[trans-4-[2-(trans-4-(3-butenyl)cyclohexyl)ethyl]-cyclohexyl]-3-chloro-4-fluorobenzene;

1-[trans-4-[2-(trans-4-(3-butenyl)cyclohexyl)ethyl]-cyclohexyl]-4-chlorobenzene;

1-[trans-4-[2-(trans-4-(3-butenyl)cyclohexyl)ethyl]-cyclohexyl]-3-fluoro4-chlorobenzene;

1-[[trans-4-(trans-4-(3butenyl)cyclohexyl)cyclohexyl]-methoxy]-4-fluorobenzene, m.p. (C-N) 82.2° C., cl.p. (N-I) 131.7° C;

1-[[trans-4-(trans-4-(3-butenyl)cyclohexyl)cyclohexyl]-methoxy]-3,4-difluorobenzene;

1-[[trans-4-(trans-4-(3-butenyl)cyclohexyl)cyclohexyl]-methoxy]-3-chloro-4-fluorobenzene;

1-[[trans-4-(trans-4-(3-butenyl)cyclohexyl)cyclohexyl]-methoxy]-4-chlorobenzene;

1-[[trans-4-(trans-4-(3-butenyl)cyclohexyl)cyclohexyl]-methoxy]-3-fluoro-4-chlorobenzene;

1-[2-[trans-4-(trans-4-(3-butenyl)cyclohexyl)cyclohexyl]ethyl]-3,4-difluorobenzene;

1-[2-[trans-4-(trans-4-(3-butenyl)cyclohexyl)cyclohexyl]ethyl]-3-chloro-4-fluorobenzene;

1-[2-[trans-4-(trans-4-(3-butenyl)cyclohexyl)cyclohexyl]ethyl]-4-chlorobenzene;

1-[2-[trans-4-(trans-4-(3-butenyl)cyclohexyl)cyclohexyl]ethyl]-3-fluoro-4-chlorobenzene;

3,4-difluorobenzoic acid trans-4-[trans-4-(3-butenyl)-cyclohexyl]cyclohexyl ester;

3-chloro-4-fluorobenzoic acid trans-4-[trans-4(3-butenyl)cyclohexyl]cyclohexyl ester; 4-chlorobenzoic acid trans-4-[trans-4-(3-butenyl)-cyclohexyl]cyclohexyl ester;

3-fluoro-4-chlorobenzoic acid trans-4-[trans-4-(3-butenyl)cyclohexyl]cyclohexyl ester;

trans-4-[trans-4-(3-butenyl)cyclohexyl]cyclohexyl 4-fluorobenzyl ether m.p. (C-N) 37.7° C., cl.p. (N-I) 92.8° C.;

trans-4-[trans-4-(3-butenyl)cyclohexyl]cyclohexyl 3,4-difluorobenzyl ether;

trans-4-[trans-4-(3-butenyl)cyclohexyl]cyclohexyl 3-chloro-4-fluorobenzyl ether;

trans-4-[trans-4-(3-butenyl)cyclohexyl]cyclohexyl 4-chlorobenzyl ether;

trans-4-[trans-4-(3-butenyl)cyclohexyl]cyclohexyl 3-fluoro-4-chlorobenzyl ether;

1-[trans-4-[trans-4-(3E-pentenyl)cyclohexyl]cyclohexyl]-3,4-difluorobenzene;

1-[trans-4-[2-(trans-4(3E-pentenyl)cyclohexyl)ethyl]-cyclohexyl]-3,4-difluorobenzene;

1-[[trans-4-(trans-4-(3E-pentenyl)cyclohexyl)cyclohexyl]methoxy]-4-fluorobenzene;

1-[[trans-4-(trans-4-(3E-pentenyl)cyclohexyl)cyclohexyl]methoxy]-3,4-difluorobenzene;

1-[2-[trans-4-(trans-4-(3E-pentenyl)cyclohexyl)cyclohexyl]ethyl]-3,4difluorobenzene;

trans-4-[trans-4-(3E-pentenyl)cyclohexyl]cyclohexyl 4-fluorobenzyl ether;

trans-4-[trans-4-(3E-pentenyl)cyclohexyl]cyclohexyl 3,4-difluorobenzyl ether;

3,4-difluorobenzoic acid trans-4-[trans-4-(3E-pentenyl)cyclohexyl]cyclohexyl ester;

trans-4-[trans-4-(3E-pentenyl)cyclohexyl]cyclohexyl 3,4difluorobenzyl ether.

EXAMPLE 10 a) A suspension of 1.20 g of lithium aluminium hydride in 50 ml of diethyl ether was treated dropwise within 15 minutes with a solution of 6.67 g of trans-4-(4-fluorophenyl)cyclohexanecarboxylic acid in 200 ml of diethyl ether and 40 ml of tetrahydrofuran. The reaction mixture was stirred at room temperature for 2 hours, then treated dropwise with 4 ml of acetone and 14 ml of water and made acid (pH about 1) with 3 N hydrochloric acid. The aqueous phase was separated. The organic phase was washed with 30 ml of water, twice with 20 ml of semi-saturated sodium carbonate solution each time and three times with 30 ml of water each time, dried over sodium sulfate and evaporated. There were thus obtained 6.08 g of crude [trans-4-(4-fluorophenyl)cyclohexyl]methanol with m.p. 65°-70° C.

b) A suspension of 11.35 g of pyridinium chlorochromate in 80 ml of dichloromethane was treated dropwise with a solution of 6.06 g of [trans-4-(4-fluorophenyl)cyclohexyl]methanol in 18 ml of diethyl ether. The reaction mixture was stirred for 4 hours, then diluted with 50 ml of diethyl ether, decanted off from the dark residue and filtered. Concentration of the filtrate gave 4.86 g of trans-4-(4-fluorophenyl)cyclohexanecarboxaldehyde as a yellowish oil which solidified at room temperature; m.p. <30° C.

EXAMPLE 11

A solution of 0.98 g of 2-(4-pentenyl)-1,3-propanediol and 1.34 g of trans-4-(4-fluorophenyl)cyclohexanecarboxaldehyde in 40 ml of toluene was treated with 4 drops of 10 percent sulfuric acid in a sulfonation flask equipped with a descending condenser. The mixture was boiled for 1 hour, with the damp solvent which was distilled off being replaced by the dropwise addition of fresh toluene. Subsequently, the reaction mixture was neutralized with triethylamine (about 8 drops), washed twice with 15 ml of water each time, dried over sodium sulfate, filtered and concentrated. Chromatographic purification of the residue (2.22 g) on silica gel with hexane/ethyl acetate (vol. 39:1) and repeated recrystallization from ethanol finally gave 0.44 g of pure trans-2-[trans-4-(4-fluorophenyl)cyclohexyl]-5-(4-pentenyl)-m-dioxane; m.p. (C-$S_B$) 68.5° C., phase transition ($S_B$-N) 77° C., cl.p. (N-I) 96.5° C.

The following compounds can be prepared in an analogous manner:

trans-2-[trans-4-(3,4-difluorophenyl)cyclohexyl]-5-(4-pentenyl)-m-dioxane;

trans-2-[trans-4-(4-chlorophenyl)cyclohexyl]-5-(4-pentenyl)-m-dioxane;

trans-2-[trans-4-(3,4-difluorophenyl)cyclohexyl]-5-(3-butenyl)-m-dioxane;

trans-2-[trans-4-(4-chlorophenyl)cyclohexyl]-5-(3-butenyl)-m-dioxane;

trans-2-[trans-4-[2-(4-fluorophenyl)ethyl]cyclohexyl]-5-(4-pentenyl)-m-dioxane;
trans-2-[trans-4-[2-(3,4-difluorophenyl)ethyl]cyclohexyl]-5-(4-pentenyl)-m-dioxane;
trans-2-[trans-4-[2-(4-chlorophenyl)ethyl]cyclohexyl]-5-(4-pentenyl)-m-dioxane;
trans-2-[trans-4-[2-(3,4-difluorophenyl)ethyl]cyclohexyl]-5-(3-butenyl)-m-dioxane;
trans-2-[trans-4-[2-(4-chlorophenyl)ethyl]cyclohexyl]-5-(3-butenyl)-m-dioxane;
trans-2-(4-fluorophenyl)-5-(4-pentenyl)-m-dioxane, m.p. (C-I) 18.7° C.;
trans-2-(3,4-difluorophenyl)-5-(4-pentenyl)-m-dioxane;
trans-2-(4-chlorophenyl)-5-(4-pentenyl()-m-dioxane;
trans-2-(3,4-difluorophenyl)-5-(3-butenyl)-m-dioxane;
trans-2-(4-chlorophenyl)-5-(3-butenyl)-m-dioxane;
trans-2-[2-(4-fluorophenyl)ethyl]-5-(4-pentenyl)-m-dioxane;
trans-2-[2-(3,4-difluorophenyl)ethyl]-5-(4-pentenyl)-m-dioxane;
trans-2-[2-(4-chlorophenyl)ethyl]-5-(4-pentenyl)-m-dioxane;
trans-2-[2-(3,4-difluorophenyl)ethyl]-5-(3-butenyl)-m-dioxane;
trans-2-[2-(4-chlorophenyl)ethyl]-5-(3-butenyl)-m-dioxane.

EXAMPLE 12

A mixture of 3.6 g of 7-dimethoxy-6-(dimethoxymethyl)-1-heptene, 75 mg of p-toluenesulfonic acid monohydrate and 0.35 ml of water was heated to slight boiling for 2 hours in an oil bath of 110° C. while stirring and under a nitrogen atmosphere. Thereafter, the mixture was treated with 0.5 g of sodium hydrogen carbonate, stirred for 10 minutes without the oil bath and then filtered (rinsing with a small amount of methanol). the filtrate was added to a solution of 2.9 g of 4-fluorobenzamidine hydrochloride in 60 ml of methanol. Subsequently, the reaction mixture was treated dropwise with a sodium methylate solution (prepared from 0.6 g of sodium and 15 ml of methanol), stirred at room temperature overnight, then adjusted to pH 5 with concentrated hydrochloric acid and evaporated. The residue was treated with water and extracted with diethyl ether. The organic phase was washed with water, dried over sodium sulfate, filtered and evaporated. Chromatographic purification of the crude product on silica gel with hexane/ethyl acetate (vol. 19:1) and recrystallization from hexane gave 1.0 g of pure 2-(4-fluorophenyl)-5-(4-pentenyl)pyrimidine with m.p. 21.8° C.

The following compounds can be prepared in an analogous manner:

2-(3,4-Difluorophenyl)-5-(4-pentenyl)pyrimidine;
2-(4-chlorophenyl)-5-(4-pentenyl)pyrimidine;
2(3,4-difluorophenyl)-5-(3-butenyl)pyrimidine;
2-(4-chlorophenyl)5-(3-butenyl)pyrimidine;
2-(4-fluorophenyl)-5-[trans-4-(4-pentenyl)cyclohexyl]-pyrimidine;
2-(3,4-difluorophenyl)-5-[trans-4-(4-pentenyl)cyclohexyl]pyrimidine;
2-(4-chlorophenyl)-5-[trans-4-(4-pentenyl)cyclohexyl]-pyrimidine;
2-(3,4-difluorophenyl)-5-[trans-4-(3-butenyl)cyclohexyl]pyrimidine;
2-(4-chlorophenyl)-5-[trans-4-(3-butenyl)cyclohexyl]-pyrimidine;
2-(4'-fluoro-4-biphenylyl)-5-(4-pentenyl)pyrimidine;
2-(3',4'-difluoro-4-biphenylyl)-5-(4-pentenyl)-pyrimidine;
2-(4'-chloro-4-biphenylyl)-5-(4-pentenyl)pyrimidine;
2-(3',4'-difluoro-4-biphenylyl)-5-(3-butenyl)pyrimidine;
2-(3'-chloro-4-biphenylyl)-5-(3-butenyl)pyrimidine.

EXAMPLE 13

The binary mixtures set forth hereinafter were prepared from 4-(trans-4-pentenylcyclohexyl)benzonitrile and a compound of formula I. The electro-optical data were measured at 22° C. in a TN cell having a plate separation of 8 -$\mu$m. The corresponding values for 4-(trans-4-pentylcyclohexyl)benzonitrile are: $V_{10}=1.62$ V, $t_{on}=30$ ms, $\Delta n=0.120$; cl.p. (N-I) 54.6° C.

Mixture 1

90 wt. % of 4-(trans-4-pentylcyclohexyl)benzonitrile,
10 wt. % of 4-(3-butenyloxy)benzoic acid 4-fluorophenyl ester;
$V_{10}=1.29$ V, $t_{on}=31$ ms, $\Delta n=0.117$.

Mixture 2

90 wt. % of 4-(trans-4-pentylcyclohexyl)benzonitrile,
10 wt. % of trans-4-(4-pentenyl)cyclohexanecarboxylic acid 4-fluorophenyl ester;
$V_{10}=1.17$ V, $t_{on}=22$ ms, $\Delta n=0.108$.

Mixture 3

70 wt. % of 4-(trans-4-pentylcyclohexyl)benzonitrile,
30 wt. % trans -4-[trans-4-(4-pentenyl)cyclohexyl]cyclohexanecarboxylic acid 4-fluorophenyl ester;
$V_{10}=1.55$ V, $t_{on}=44$ ms, $\Delta n=0.110$; cl.p. (N-I) 75.3° C.

Mixture 4

90 wt. % of 4-(trans-4-pentylcyclohexyl)benzonitrile,
10 wt. % of 4-(4-pentenyl)benzoic acid 4-fluorophenyl ester;
$V_{10}=1.42$ V, $t_{on}=26$ ms, $\Delta n=0.117$, cl.p. (N-I) 50.3° C.

Mixture 5

90 wt. % of 4-(trans-4-pentylcyclohexyl)benzonitrile,
10 wt. % of 4-(3-butenyloxy)benzoic acid 3,4-difluorophenyl ester;
$V_{10}=1.23$ V, $t_{on}=36$ ms, $\Delta n=0.116$, cl.p. (N-I) 44.5° C.

Mixture 6

90 wt. % of 4-(trans-4-pentylcyclohexyl)benzonitrile,
10 wt. % of 1-[trans-4-[trans-4-(4-pentenyl)cyclohexyl]cyclohexyl]-4-fluorobenzene;
$V_{10}=1.47$ V, $t_{on}=25$ ms, $\Delta n=112$, cl.p. (N-I) 59.1° C.

Mixture 7

90 wt. % of 4-(trans-4-pentylcyclohexyl)benzonitrile,
10 wt. % of trans-2-[trans-4-(4-fluorophenyl)cyclohexyl]-5-(4-pentenyl)-m-dioxane;
$V_{10}=1.34$ V, $t_{on}=31$ ms, $\Delta n=1.116$. cl.p. (N-I) 54.0° C.

EXAMPLE 14

The following mixtures were prepared. Unless stated otherwise, the electro-optical data were measured at 22° C. in a TN cell having a plate separation of 6 -$\mu$m.

Mixture A 15 wt. % of trans-4-[trans-4-(3-butenyl)cyclohexyl]-cyclohexanecarbonitrile, 12 wt. % of trans-4-[trans-4-(3E-pentenyl)cyclohexyl]cyclohexanecarbonitrile, 10 wt. % of trans-4-[trans-4-(4pentenyl)cyclohexyl]-cyclohexanecarbonitrile, 10 wt. % of 4-[trans-4-(1E-propenyl)cyclohexyl]benzonitrile, 20 wt. % of trans-4-allyloxy-1-(trans-4-propylcyclohexyl)-cyclohexane, 15 wt. % of 4-ethoxy-1-[trans-4-(3E-pentenyl)cyclohexyl]-benzene, 10 wt. % of trans-4-[trans-4-(3-butenyl)cyclohexyl]-cyclohexanecarboxylic acid 4-fluorophenyl ester.

8 wt. % of trans-4-[trans-4-(4-pentenyl)cyclohexyl]-cyclohexanecarboxylic acid 4-fluorophenyl ester;

m.p. $< -30°$ C., cl.p. (N-I) $71°$ C.; $V_{10}=2.10$ V, $p=0.204$, $t_{on}=19$ ms, $t_{off}=31$ ms, $\Delta n=0.084$.

Mixture B 15 wt. % of trans-4-[trans-4-(3-butenyl)cyclohexyl]-cyclohexanecarbonitrile, 12 wt. % of trans-4-[trans-4-(3E-pentenyl)cyclohexyl]cyclohexanecarbonitrile, 10 wt. % of trans-4-[trans-4-(4-pentenyl)cyclohexyl]-cyclohexanecarbonitrile, 33 wt. % of trans-4-allyloxy-1-(trans-4-propylcyclohexyl)cyclohexane, 20 wt. % of trans-4-[trans-4-(3-butenyl)cyclohexyl]-cyclohexanecarboxylic acid 4-fluorophenyl ester, 10 wt. % of trans-4-[trans-4-(4-pentenyl)cyclohexyl]-cyclohexanecarboxylic acid 4-fluorophenyl ester;

m.p. $< -20°$ C., cl.p. (N-I) $81°$ C.; $V_{10}=2.41$ V, $p=0.211$, $t_{on}=24$ ms, $t_{off}=37$ ms, $\Delta n=0.67$.

Mixture C 10 wt. % of 4-[trans-4-(1E-propenyl)cyclohexyl]benzonitrile, 15 wt. % of 4-ethoxy-1-[trans-4-(3E-pentenyl)cyclohexyl]-benzene.

12 wt. % of trans-4-[trans-4-(3-butenyl)cyclohexyl]-cyclohexanecarbonitrile, 10 wt. % of trans-4-[trans-4(3E-pentenyl)cyclohexyl]cyclohexanecarbonitrile, 8 wt. % of trans-4-[trans-4(4-pentenyl)cyclohexyl]cyclohexanecarbonitrile, 15 wt. % of trans-4-(3-butenyl)-1-(trans-4-ethoxycyclohexyl)-cyclohexane, 8 wt. % of 1-[2-(trans-4-butylcyclohexyl)ethyl]-4-(trans-4-pentylcyclohexyl)benzene, 8 wt. % of trans-4-[trans-4-(3-butenyl)cyclohexyl]cyclohexanecarboxylic acid 4-fluorophenyl ester, 8 wt. % of trans-4-[trans-4-(3E-pentenyl)cyclohexyl]cyclohexanecarboxylic acid 4-fluorophenyl ester, 6 wt. % of trans-4-[trans-4(4-pentenyl)cyclohexyl]cyclohexanecarboxylic acid 4-fluorophenyl ester;

m.p. $< -30°$ C., cl.p. $84°$ C. nematic; $V_{10}=2.35$ V; $t_{on}$ (22° C.)=15 ms, $t_{on}(-20°$ C.)=309 ms, $t_{off}$(22° C.)=27 ms, $t_{off}(-20°$ C.)=420 ms; $\Delta n=0.088$.

Mixture D 10 wt. % of 4-]trans-4-(1E-propenyl)cyclohexyl]benzonitrile, 6 wt. % of 4-[trans-4-(3E-propenyl)cyclohexyl]benzonitrile, 12 wt. % of 4-ethoxy-1-[trans-4-(3E-pentenyl)cyclohexyl]-benzene, 5 wt. % of trans-4-[trans-4-(3E-butenyl)cyclohexyl]-cyclohexanecarbonitrile, 7 wt. % of trans-4-[trans-4-(3E-pentenyl)cyclohexyl]-cyclohexanecarbonitrile, 12 wt. % of trans-4-allyloxy-1-(trans-4-propylcyclohexyl)-cyclohexane, 10 wt. % of trans-4-(3E-pentenyl)-1(trans-4-ethoxycyclohexyl)cyclohexane, 6wt. % of 4-[trans-4-(3E-pentenyl)cyclohexyl]-4'-propylbiphenyl.

6 wt. % of trans-4-propylcyclohexanecarboxylic acid 4-[trans-4-(3E-pentenyl)cyclohexyl]phenyl ester, 10 wt. % of 1-[2-(trans-4-butylcyclohexyl)ethyl]-4-(trans-4-pentylcyclohexyl) benzene, 4wt. % of 4-[2-(trans-4-butylcyclohexyl)ethyl]-4'-[trans-4-(3E-pentenyl)cyclohexyl]biphenyl, 8 wt. % of trans-4-[trans-4-(3-butenyl)cyclohexyl]cyclohexanecarboxylic acid 4-fluorophenyl ester, 4 wt. % of trans-4-[trans-4-(3E-pentenyl)cyclohexyl]-cyclohexanecarboxylic acid 4-fluorophenyl ester;

m.p.$< -30°$ C., cl.p. $100°$ C. nematic; $V_{10}=2.82$ V; $t_{on}$ (22° C.)=12 ms, $t_{on}=(-20°$ C.)=220 ms, $t_{off}$ (22° C.)=21 ms, $t_{off}(-20°$ C.)=330 ms; $\Delta n=0.105$.

Mixture E 9.40 wt. % of 4-[trans-4-(1E-propenyl)cyclohexyl]-benzonitrile, 5.64 wt. % of 4-[trans-4-(3E-pentenyl)cyclohexyl]-benzonitrile, 11.28 wt. % of 4-ethoxy-1-[trans-4-(3E-pentenyl)cyclohexyl]benzene, 4.70 wt. % of trans-4-[trans-4-(3-butenyl)cyclohexyl]-cyclohexanecarbonitrile, 6.58 wt. % of trans-4-[trans-4-(3E-pentenyl)cyclohexyl]-cyclohexanecarbonitrile, 11.28 wt. % of trans-4-allyloxy-1-(trans-4-propylcyclohexyl)-cyclohexane, 9.40 wt. % of trans-4-(3E-pentenyl)-1-(trans-4-ethoxycyclohexyl)cyclohexane, 6.00 wt. % of 2-cyano-5-(trans-4-butylcyclohexyl)-pyrimidine, 5.65 wt. % of trans-4-propylcyclohexanecarboxylic acid 4-[trans-4-(3E-pentenyl)cyclohexyl]phenyl ester.

5.64 wt. % of 4-[trans-4-(3-pentenyl)cyclohexyl]-4'-propylbiphenyl, 9.40 wt. % of 1-[2-(trans-4-butylcyclohexyl)ethyl]-4-trans-4-pentylcyclohexyl)benzene, 3.76 wt. % of 4-[2-(trans-4-butylcyclohexyl)ethyl]-4'-[trans-4-(3E-pentenyl)cyclohexyl]biphenyl, 7.52 wt. % of trans-4-[trans-4-(3-butenyl)cyclohexyl]-cyclohexanecarboxylic acid 4-fluorophenyl ester, 3.76 wt. % of trans-4-[trans-4-(3E-pentenyl)cyclohexyl]-cyclohexanecarboxylic acid 4-fluorophenyl ester;

m.p.$< -30°$ C., cl.p. $95°$ C. nematic; $V_{10}=2.35$ V; $t_{on}$ (22° C.)=16 ms, $t_{on}=(-20°$ C.)=300 ms, $t_{off}$ (22° C.)=24 ms, $t_{off}(-20°$ C.)=350 ms; $\Delta n=0.104$.

Mixture F 10 wt. % of 4-[trans-4-(1E-propenyl)cyclohexyl]benzonitrile, 12 wt. % of 4-(2E-butenyloxy)-1-(trans-4-propylcyclohexyl)-benzene, 5 wt. % of trans-4-[trans-4-(3-butenyl)cyclohexyl]cyclohexanecarbonitrile, 7 wt. % of trans-4-[trans-4-(3E-pentenyl)cyclohexyl]-cyclohexanecarbonitrile, 6 wt. % of trans-4-[trans-4-(4-pentenyl)cyclohexyl]-cyclohexanecarbonitrile, 12 wt. % of trans-4-allyloxy-1-(trans-4-propylcyclohexyl)-cyclohexane, 10 wt. % of trans-4-(3E-pentenyl)-1-(trans-4-ethoxycyclohexyl)cyclohexane, 8 wt. % of trans-4-propylcyclohexanecarboxylic acid 4[trans-4-(3E-pentenyl)cyclohexyl]phenyl ester, 10 wt. % of 1-[2-(trans-4-butylcyclohexyl)ethyl]-4-(trans-4-pentylcyclohexyl)benzene, 5 wt. % of 4-[2-(trans-4-butylcyclohexyl)ethyl]-4'-(trans-4-pentylcyclohexyl)biphenyl, 3 wt. % of 5-(trans-4-pentylcyclohexyl)-2-[4-(trans-4-propylcyclohexyl)phenyl]pyrimidine, 4 wt. % of trans-4-[trans-4-(3-butenyl)cyclohexyl]cyclohexanecarboxylic acid 4-fluorophenyl ester, 8 wt. % of trans-4-[trans-4-(3E-pentenyl)cyclohexyl]cyclohexanecarboxylic acid 4-fluorophenyl ester;

m.p.<−30° C., cl.p. 109° C. nematic; $V_{10}$=2.84 V; $t_{on}$ (22° C.)=16 ms, $t_{on}$=(−20° C.)=336 ms, $t_{off}$ (22° C.)=26 ms, $t_{off}$(−20° C.)=370 ms; $\Delta n$=0.096.

Mixture G 10 wt. % of 4-(trans-4-propylcyclohexyl)benzonitrile, 8 wt. % of 4-[trans-4-(1E-propenyl)cyclohexyl]benzonitrile, 10 wt. % of trans-4-(trans-4-vinylcyclohexyl)cyclohexanecarbonitrile, 8 wt. % of trans-4-[trans-4-(3E-pentenyl)cyclohexyl]cyclohexanecarbonitrile, 10 wt. % of trans-4-ethoxy-1-[trans-4-(3E-pentenyl)cyclohexyl]cyclohexane, 8 wt. % of trans-4-ethoxy-1-[trans-4-(4-pentenyl)cyclohexyl]cyclohexane, 8 wt. % of 2-cyano-5-(trans-4-butylcyclohexyl)-pyrimidine, 3 wt. % of 2-cyano-5-(trans-4-pentylcyclohexyl)-pyrimidine, 7 wt. % of 4-(2E-butenyloxy)-1-[trans-4-(trans-4-propylcyclohexyl)cyclohexyl]benzene, 5 wt. % of trans-4-[5-(trans-4-butylcyclohexyl)-2-pyrimidinyl]cyclohexanecarbonitrile, 8 wt. % of trans-4-propylcyclohexanecarboxylic acid 4-[trans-4-(3E-pentenyl)cyclohexyl]phenyl ester, 7 wt. % of 1-[trans-4-(trans-4-propylcyclohexyl)cyclohexyl]-4-fluorobenzene, 5 wt. % of trans-4-[trans-4-(3-butenyl)cyclohexyl]cyclohexanecarboxylic acid 4-fluorophenyl ester, 7 wt. % of trans-4-[trans-4-(4-pentenyl)cyclohexyl]cyclohexanecarboxylic acid 4-fluorophenyl ester;

m.p.<−30° C., cl.p. 92° C., nematic; $V_{10}$=1.71 V; $t_{on}$ (22° C.)=19 ms, $t_{on}$=(−20° C.)=530 ms, $t_{off}$ (22° C.)=34 ms, $t_{off}$(−20° C.)=720 ms; $\Delta n$=0.094.

Mixture H 7 wt. % of 4-(trans-4-propylcyclohexyl)benzonitrile, 8 wt. % of 4-[trans-4-(1E-propenyl)cyclohexyl]benzonitrile, 10 wt. % of trans-4-(trans-4-vinylcyclohexyl)cyclohexanecarbonitrile, 10 wt. % of trans-4-methoxy-1-[trans-4-(3E-pentenyl)cyclohexyl]-cyclohexane, 10 wt. % of trans-4-ethoxy-1-[trans-4-(3-butenyl)cyclohexyl]-cyclohexane, 12 wt. % of trans-4-ethoxy-1-[trans-4-(3E-pentenyl)-cyclohexyl]cyclohexane, 8 wt. % of 1-[2-(trans-4-butylcyclohexyl)ethyl]-4-(trans-4-pentylcyclohexyl)benzene, 6 wt. % of trans-4-propylcyclohexanecarboxylic acid 4-[trans-4-(3E-pentenyl)cyclohexyl]phenyl ester, 8 wt. % of 1-[trans-4-(trans-4-propylcyclohexyl)cyclohexyl]-4-fluorobenzene, 6 wt. % of 1-[trans-4-(trans-4-vinylcyclohexyl)cyclohexyl]-4-fluorobenzene, 4 wt. % of 4-[2-(trans-4-butylcyclohexyl)ethyl]-4'-[trans-4-(3E-pentenyl)cyclohexyl]biphenyl, 3 wt. % of 5-(trans-4-pentylcyclohexyl)-2-[4-(trans-4-propylcyclohexyl)phenyl]pyrimidine, 8 wt. % of trans-4-(4-pentenyl)cyclohexanecarboxylic acid 4-fluorophenyl ester;

m.p.<−30° C., cl.p. 88° C., nematic; $V_{10}$=2.29 V; $t_{on}$ (22° C.)=12 ms, $t_{on}$ (−20° C.)=221 ms, $t_{off}$ (22° C.)=23 ms, $t_{off}$(−20° C.)=296 ms; $\Delta n$=0.080.

Mixture I 7 wt. % of 4-(trans-4-propylcyclohexyl)benzonitrile, 8 wt. % of 4-(trans-4-(1E-propenyl)cyclohexyl)benzonitrile, 10 wt. % of trans-4-(trans-4-vinylcyclohexyl)cyclohexanecarbonitrile 10 wt. % of trans-4methoxy-1-[trans-4-(3E-pentenyl)-cyclohexyl]cyclohexane, 10 wt. % of trans-4-ethoxy-1-[trans-4-(3-butenyl)cyclohexyl]-cyclohexane, 12 wt. % of trans-4-ethoxy-1-[trans-4-(3E-pentenyl)-cyclohexyl]cyclohexane, 8 wt. % of 1-[2-(trans-4-butylcyclohexyl)ethyl]-4-(trans-4-pentylcyclohexyl)benzene, 6 wt. % of trans-4-propylcyclohexanecarboxylic acid 4-[trans-4-(3E-pentenyl)cyclohexyl]phenyl ester, 8 wt. % of 1-[trans-4-(trans-4-propylcyclohexyl)cyclohexyl]-4-fluorobenzene, 6 wt. % of 1-[trans-4-(trans-4-vinylcyclohexyl)cyclohexyl]-4-fluorobenzene, 4 wt. % of 4-[2-(trans-4-butylcyclohexyl)ethyl]-4'-[trans-4-(3E-pentenyl)cyclohexyl]biphenyl, 3 wt. % of 5-(trans-4-pentylcyclohexyl)-2-[4-(trans-4-propylcyclohexyl)phenyl]pyrimidine, 8 wt. % of trans-2-(4-fluorophenyl)-5-(4-pentenyl)-m-dioxane;

m.p.<−30° C., cl.p. 81° C., nematic; $V_{10}$=2.15 V, $t_{on}$ (22° C.)=14 ms, $t_{on}$=(−20° C.)=249 ms, $t_{off}$ (22° C.)=26 ms, $t_{off}$(−20° C.)=342 ms; $\Delta n$=0.087.

Mixture J 10 wt. % of 4-[(trans-4-propylcyclohexyl)benzonitrile, 7 wt. % of 4-[(trans-4-vinylcyclohexyl)benzonitrile, 8 wt. % of 4-[(trans-4-(1E-propenyl)cyclohexyl]benzonitrile, 6 wt. % of 4-ethoxy-1-(trans-4-propylcyclohexyl)-benzene, 10 wt. % of trans-4-methoxy-1-[trans-4-(3E-pentenyl)cyclohexyl]cyclohexane, 10 wt. % of trans-4-ethoxy-1-[trans-4-(3-butenyl)cyclohexyl)-cyclohexane, 12 wt. % of trans-4-ethoxy-1-[trans-4-(3E-pentenyl)-cyclohexyl]cyclohexane, 8 wt. % of 4-(2E-butenyloxy)-1-[trans-4-(trans-4-propylcyclohexyl)cyclohexyl]benzene, 8 wt. % of 1-[2-(trans-4-butylcyclohexyl)ethyl]-4-(trans-4-pentylcyclohexyl)benzene, 6 wt. % of trans-4-propylcyclohexanecarboxylic acid 4-[trans-4-(3E-pentenyl)cyclohexyl]phenyl ester, 4 wt. % of 4,4'-bis-(trans-4-propylcyclohexyl)biphenyl, 3 wt. % of 5-(trans-4-pentylcyclohexyl)-2-[4-(trans-4-propylcyclohexyl)phenyl]pyrimidine, 8 wt. % of trans-4-[trans-4-(4-pententyl)cyclohexyl]-cyclohexanecarboxylic acid 4-fluorophenyl ester;

m.p.<−30° C., cl.p. 95° C., nematic; $V_{10}$=2.41 V, $t_{on}$ (22° C.)=12 ms, $t_{on}$ (−20° C.)=195 ms, $t_{off}$ (22° C.)=21 ms, $t_{off}$(−20° C.)=276 ms; Δn=0.101.

We claim:

1. A compound of the formula

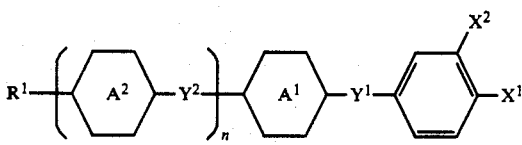

I wherein $X^1$ is fluorine or chlorine and $X^2$ is fluorine or chlorine; $R^1$ is $C_4$–$C_{15}$ 3E-alkenyl, $C_5$–$C_{15}$ 4-alkenyl, $C_3$–$C_{14}$ 2E-alkenyloxy or $C_4$–$C_{14}$ 3-alkenyloxy; n is the integer 0 or 1; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and each of rings $A^1$ and $A^2$ individually is trans-1,4-cyclohexylene, trans-1,4-cyclohexylene in which 2 non-adjacent CH$_2$ groups are replaced by oxygen, 1,4-phenylene, or 1,4-phenylene in which 1 CH group of 2 CH groups is/are replaced by nitrogen, the above rings $A^1$ and $A^2$ being unsubstituted or substituted with at least one of cyano, lower alkyl or halo.

2. The compound of claim 1, wherein ring $A^1$ is substituted or unsubstituted trans-1,4-cyclohexylene, substituted or unsubstituted 1,4-phenylene or pyridine-2,5-diyl, pyrimidine-2,5-diyl or pyrazine-2,5-diyl.

3. The compound of claim 1, wherein ring $A^2$ is substituted or unsubstituted trans-1,4-cyclohexylene, substituted or unsubstituted 1,4-phenylene or, when ring $A^1$ is substituted or unsubstituted trans-1,4-cyclohexylene or substituted or unsubstituted 1,4-phenylene, ring $A^2$ also can be pyrimidine-2,5-diyl or trans-m-dioxane-2,5-diyl.

4. The compound of claim 1, wherein ring $A^1$ is trans-1,4-cyclohexylene, 1,4-phenylene, pyridine-2,5-diyl, pyrimidine-2,5-diyl or pyrazine-2,5-diyl and ring $A^2$ is trans-1,4-cyclohexylene.

5. The compound of claim 1, having the formula

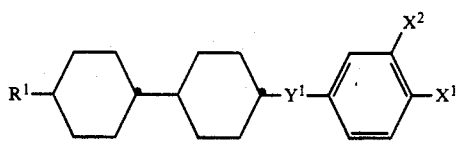

I-23 wherein $R^1$, $X^1$, $X^2$ and $Y^1$ have the significances given in claim 1.

6. The compound of claim 1, wherein $X^1$ and $X^2$ are fluorine.

7. The compound of claim 1, wherein $R^1$ is a unbranched residue having the significance given in claim 1.

8. An electro-optical cell comprising:
(a) two plate means;
(b) liquid crystal means disposed between the two plate means and including a compound of the formula:

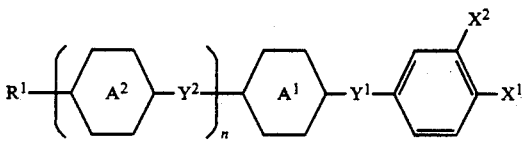

I wherein $X^1$ is fluorine or chlorine and $X^2$ is fluorine or chlorine; $R^1$ is $C_4$–$C_{15}$ 3E-alkenyl, $C_5$–$C_{15}$ 4-alkenyl, $C_3$–$C_{14}$ 2E-alkenyloxy or $C_4$–$C_{14}$ 3-alkenyloxy; n is the integer 0 or 1; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and each of rings $A^1$ and $A^2$ individually is trans-1,4-cyclohexylene, trans-1,4-cyclohexylene in which 2 non-adjacent CH$_2$ groups are replaced by oxygen, 1,4-phenylene, or 1,4-phenylene in which 1 CH group or 2 CH groups is/are replaced by nitrogen, the above rings $A^1$ and $A^2$ being unsubstituted or substituted with at least one of cyano, lower alkyl or halo; and
(c) means for applying an electrical potential to said plate means.

9. A compound of claim 1 wherein in formula I, $R^1$ is 3-butenyl, $A^1$ and $A^2$ each are trans-1,4-cyclohexylene, $Y^1$ and $y^2$ are each a single covalent bond, n is 1, and $X^1$ and $X^2$ are each fluorine.

* * * * *